(12) United States Patent
Mermod et al.

(10) Patent No.: US 7,129,062 B2
(45) Date of Patent: Oct. 31, 2006

(54) MATRIX ATTACHMENT REGIONS AND METHODS FOR USE THEREOF

(75) Inventors: Nicolas Mermod, Buchillon (CH); Monique Zahn-Zabal, Lausanne (CH); Markus Imhof, Chexbres (CH); Philippe Chatellard, Lausanne (CH); Pierre-Alain Girod, Lausanne (CH)

(73) Assignee: Selexis SA, Geneva (CH)

( * ) Notice: Subject to any disclaimer, the term of this patent is extended or adjusted under 35 U.S.C. 154(b) by 555 days.

(21) Appl. No.: 10/059,561

(22) Filed: Jan. 28, 2002

(65) Prior Publication Data

US 2003/0087342 A1  May 8, 2003

Related U.S. Application Data

(60) Provisional application No. 60/281,391, filed on Apr. 4, 2001, provisional application No. 60/264,355, filed on Jan. 26, 2001.

(51) Int. Cl.
C12P 21/06 (2006.01)
C12N 15/63 (2006.01)
C12N 15/74 (2006.01)
C12N 15/00 (2006.01)
C12N 5/02 (2006.01)
C07H 21/04 (2006.01)

(52) U.S. Cl. .......... 435/69.1; 435/455; 435/320.1; 435/326; 536/23.53; 536/24.1

(58) Field of Classification Search .......... 435/69.1, 435/455, 320.1, 326, 471; 536/23.53
See application file for complete search history.

(56) References Cited

U.S. PATENT DOCUMENTS

| | | | |
|---|---|---|---|
| 5,464,758 A * | 11/1995 | Gossen et al. ............. 435/69.1 |
| 5,610,053 A * | 3/1997 | Chung et al. ............... 435/461 |
| 5,773,695 A * | 6/1998 | Thompson et al. ......... 800/293 |
| 5,831,063 A * | 11/1998 | Hughes-Jones .......... 536/23.53 |
| 5,907,078 A * | 5/1999 | Greenberg et al. ........... 800/10 |
| 6,043,077 A * | 3/2000 | Barber et al. ............... 435/236 |
| 6,252,058 B1 * | 6/2001 | Thompson ................. 536/24.1 |
| 6,388,066 B1 | 5/2002 | Bruce et al. ............... 536/24.1 |
| 6,410,314 B1 | 6/2002 | Baiker et al. ............ 435/320.1 |
| 6,426,446 B1 | 7/2002 | McElroy et al. ............ 800/278 |
| 6,429,357 B1 | 8/2002 | McElroy et al. ............ 800/278 |
| 6,437,217 B1 | 8/2002 | McElroy et al. ............ 800/278 |
| 6,521,449 B1 | 2/2003 | Polack et al. ............ 435/320.1 |
| 6,537,542 B1 | 3/2003 | Treco et al. ............. 424/93.21 |
| 6,565,844 B1 | 5/2003 | Treco et al. ............. 424/93.21 |
| 6,569,681 B1 | 5/2003 | Ivanov ...................... 435/463 |
| 6,573,429 B1 | 6/2003 | Shinmyo et al. ............ 800/287 |
| 6,583,338 B1 | 6/2003 | McElroy et al. ............ 800/287 |
| 6,596,514 B1 | 7/2003 | Morris et al. .............. 435/69.1 |
| 6,635,806 B1 | 10/2003 | Kriz et al. .................. 800/287 |
| 6,649,373 B1 | 11/2003 | Brough et al. ............. 435/69.1 |
| 6,660,521 B1 | 12/2003 | Brough et al. ........... 435/320.1 |
| 6,706,470 B1 | 3/2004 | Choo et al. ..................... 435/5 |
| 6,730,826 B1 | 5/2004 | Wagner et al. .............. 800/287 |
| 6,747,189 B1 | 6/2004 | McElroy et al. ............ 800/287 |
| 6,783,756 B1 | 8/2004 | Bujard et al. ............ 424/93.21 |
| 6,821,775 B1 | 11/2004 | Kovesdi et al. .......... 435/320.1 |
| 6,897,066 B1 | 5/2005 | Harrington .................. 435/455 |
| 2002/0001579 A1 | 1/2002 | Hillgenberg et al. ..... 424/93.21 |
| 2002/0068362 A1 | 6/2002 | Murray et al. .............. 435/456 |
| 2002/0073448 A1 | 6/2002 | Michalowski et al. ... 800/317.3 |
| 2002/0094967 A1 * | 7/2002 | Antoniou et al. ............. 514/44 |
| 2002/0098475 A1 | 7/2002 | Luo et al. ....................... 435/5 |
| 2002/0103148 A1 | 8/2002 | Agarwal et al. ............... 514/44 |
| 2003/0018997 A1 | 1/2003 | Conkling et al. ........ 800/317.3 |
| 2003/0032597 A1 | 2/2003 | Sebestyen ..................... 514/12 |
| 2003/0054548 A1 | 3/2003 | Kalenko et al. ............. 435/325 |
| 2003/0082552 A1 | 5/2003 | Wolffe et al. ................... 435/6 |
| 2003/0100077 A1 | 5/2003 | Korte et al. ................ 435/91.2 |
| 2003/0140363 A1 | 7/2003 | Rapp ........................... 800/19 |
| 2003/0140364 A1 | 7/2003 | Hinchey et al. ............ 800/278 |
| 2003/0157715 A1 | 8/2003 | Laemmli ..................... 435/455 |
| 2003/0224477 A1 | 12/2003 | Heartlein et al. .......... 435/69.1 |
| 2003/0228612 A1 | 12/2003 | Kenward et al. ............... 435/6 |
| 2003/0232414 A1 | 12/2003 | Moore ........................ 435/69.1 |
| 2004/0016015 A1 | 1/2004 | Nguyen et al. ............. 800/278 |
| 2004/0038394 A1 | 2/2004 | Kim et al. ................ 435/320.1 |
| 2004/0072352 A1 | 4/2004 | Kim et al. .................. 435/456 |
| 2004/0076954 A1 | 4/2004 | Caldwell et al. ................ 435/6 |
| 2004/0077842 A1 * | 4/2004 | Himawan ............... 530/388.22 |
| 2004/0088764 A1 | 5/2004 | Gleba et al. ................. 800/288 |
| 2004/0103454 A1 | 5/2004 | Conkling et al. ........... 800/279 |
| 2004/0115776 A1 | 6/2004 | Simesen et al. ........... 435/69.6 |

(Continued)

FOREIGN PATENT DOCUMENTS

EP 0 663 921 B1  5/2002

(Continued)

OTHER PUBLICATIONS

Tatsuka et al, An Improved Method of Electroporation for Introducing Biologically Active Foreign Genes into Cultured Mammalian Cells, Exp Cell Res, 1988, vol. 178 pp. 154-162.*

(Continued)

*Primary Examiner*—Dave Trong Nguyen
*Assistant Examiner*—Maria Marvich
(74) *Attorney, Agent, or Firm*—Mintz, Levin, Cohn, Ferris, Glovsky and Popeo, P.C.; Ivor R. Elrifi; Christina K. Stock

(57) ABSTRACT

The present invention relates to compositions and methods for transfecting eukaryotic cells with nucleic acid vectors. In particular, the invention relates to the uses of Matrix Attachment Region (MAR) elements to increase stable and transient transfection efficiency.

12 Claims, 11 Drawing Sheets

U.S. PATENT DOCUMENTS

| | | | |
|---|---|---|---|
| 2004/0126883 A1 | 7/2004 | Liu | 435/455 |
| 2004/0216189 A1 | 10/2004 | Houmard et al. | 800/287 |
| 2004/0221330 A1 | 11/2004 | Kimyuk et al. | 800/278 |
| 2004/0242512 A1 | 12/2004 | Misawa et al. | 514/44 |
| 2005/0022262 A1 | 1/2005 | Vance | 800/278 |
| 2005/0034187 A1 | 2/2005 | Golovko et al. | 800/278 |
| 2005/0050581 A1 | 3/2005 | Harvey et al. | 800/19 |
| 2005/0064467 A1 | 3/2005 | Ivanova et al. | 435/6 |
| 2005/0129669 A1 | 6/2005 | Treco et al. | 424/93.21 |
| 2005/0130267 A1 | 6/2005 | Wolffe et al. | 435/69.1 |

FOREIGN PATENT DOCUMENTS

| | | |
|---|---|---|
| EP | 1 135 512 B1 | 10/2004 |
| EP | 1 471 144 A1 | 10/2004 |
| FR | 2 832 423 A1 | 5/2003 |
| WO | WO 97/27207 | 7/1997 |
| WO | WO 97/46687 | 12/1997 |
| WO | WO 00/05393 | 2/2000 |
| WO | WO 00/32800 | 6/2000 |
| WO | WO 02/00262 A2 | 1/2002 |
| WO | WO 02/09507 A1 | 2/2002 |
| WO | WO 02/068669 A2 | 9/2002 |
| WO | WO 02/072138 A1 | 9/2002 |
| WO | WO 02/077180 A2 | 10/2002 |
| WO | WO 03/024199 A2 | 3/2003 |
| WO | WO 03/043415 A1 | 5/2003 |
| WO | WO 04/053106 A2 | 6/2004 |
| WO | WO 04/053137 A2 | 6/2004 |
| WO | WO 04/055182 A1 | 7/2004 |
| WO | WO 04/070040 A1 | 8/2004 |
| WO | WO 04/094640 A1 | 11/2004 |
| WO | WO 04/106375 A1 | 12/2004 |
| WO | WO 05/021765 A2 | 3/2005 |
| WO | WO 05/040384 A1 | 5/2005 |

OTHER PUBLICATIONS

Condreay et al, transient and stable gene expression in mammalian cells transduced with a recombinant baculovirus vector, PNAS, Jan. 1999, vol. 96, pp. 127-132.*
Southgate et al, Transcriptional Targeting to Anterior Pituitary Lactotrophic Cells Using Recombinant Adenovirus Vectors in Vitro and in Vivo in Normal and Estrogen/Sulpiride-Induced Hyperplasic Anterios Pituitaries, Endocr, 2000, vol. 141 pp. 3493-3505.*
Agarwal et al. (1998). *J. Virol.* 72: 3720-3728.
Allen et al. (1996). *The Plant Cell* 8: 899-913.
Bell and Felsenfeld (1999). *Curr. Opin. Genet. Dev.* 9: 191-198.
Bi and Broach (1999). *Genes Dev 13*: 1089-1101.
Bode et al. (2000). *Crit. Rev. Eukaryot Gene Expr. 10*: 73-90.
Bode etal. In *S/MAR Structural Properties* Academic Press Inc. 1995, pp. 389-454.
Boussif et al. (1995). *Proc. Natl. Acad. Sci. USA 92*:7297-7301.
Castilla et al. (1998). *Nat. Biotechnol. 16*: 349-354.
Cuvier et al. (1998). *Mol. Cell. Biol. 18*: 7478-7486.
Fussenegger et al. (1999). *TIBTECH 17*: 35-42.
Grosveld (1999). *Curr. Opin. Genet. Dev. 9*: 152-157.
Hart and Laemmli (1998). *Curr. Opin. Genet. Dev.* 8: 519-525.
Imhof et al. (2000). *J. Gene Med. 2*: 107-116.
Jenuwein et al. (1997). *Nature 385*: 269-272.
Jordan et al. (1996). *Nucleic Acids Res 24*: 596-601.
Kalos and Fournier (1995). *Mol. Cell. Biol. 15*: 198-207.
Kaufman and Sharp (1982). *J. Mol. Biol. 159*: 601-621.
Kiehr et al. (1991). *Biochemistry 30*: 1264-1270.
MacGregor and Caskey (1989). *Nucleic Acids Res 17*: 2365.
McKnight et al. (1992). *Proc. Natl. Acad. Sci. USA 89*: 6943-6947.
Miescher et al. (2000). *Brit. J. Haematol. 111*: 157-166.
Neff et al. (1997). *Stem Cells 15*(Supp.1): 265-271.
Ortiz et al. (1997). *EMBO J. 16*: 5037-5045.
Pawliuk et al. (1998). *Ann. NY Acad. Sci. 850*: 151-162.
Phi-Van and Stratling (1988). *EMBO J. 7*: 655-664.
Phi-Van et al. (1990). *Mol. Cell. Biol. 10*: 2302-2307.
Piechaczek et al. (1999). *Nucleic Acids Res 27*: 426-428.
Poljak et al. (1994). *Nucleic Acids Res 22*: 4386-4394.
Stief et al. (1989). *Nature 341*: 343-345.
Talbot et al. (1994). *Nucleic Acids Res 22*:756-766.
Udvardy (1999). *EMBO J. 18*: 1-8.
Urlaub et al. (1983). *Cell 33*: 405-412.
Walters et al. (1999). *Mol. Cell. Biol. 19*: 3714-3726.
Wang et al. (1997). *Nature Biotechnol. 15*: 239-243.
Wells et al. (1999). *Transgenic Research 8*: 371-381.
Zahn-Zabal et al. (2001). *J. Biotechnol. 87*: 29-42.
Greenberg, et al. (1994). "The rat probasin gene promoter directs hormonally and developmentally regulated expression of a heterologous gene specifically to the prostate in transgenic mice." *Molecular Endocrinology.* 8(2): 230-9.
Gorman, et al. (1983). "Expression of recombinant plasmids in mammalian cells is enhanced by sodium butyrate." *Nucleic Acids Research 11*(21): 7631-48.
Chen. et al. (1998). "Cointegration of DNA molecules introduced into mammalian cells by electroporation." *Somatic Cell and Molecular Genetics.* 24(4): 249-56.
EMBL Accession No. X52989, created Jul.16, 1990.
EMBL Accession No. X84223, created Feb. 11, 1995.
EMBL Accession No. X98408, created Jul. 14, 1996.
EMBL Accession No. AJ277960, created May 17, 2000.

* cited by examiner

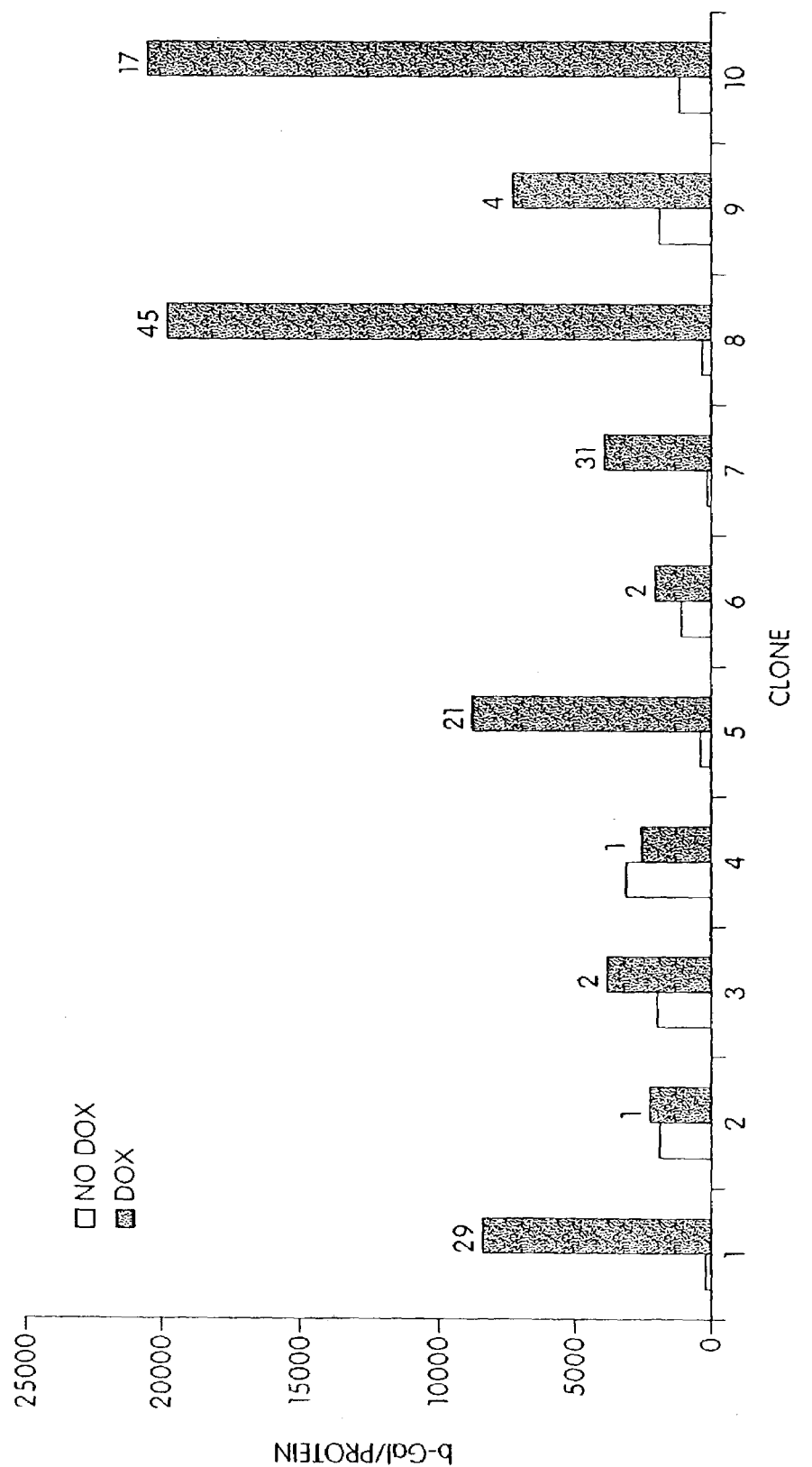

SEQUENCE LISTING

```
<160> NUMBER OF SEQ ID NOS: 9

<210> SEQ ID NO 1
<211> LENGTH: 2957
<212> TYPE: DNA
<213> ORGANISM: Gallus gallus

<400> SEQUENCE: 1
tctagaaaac aatatatttc caaatgaaaa aaaaatctga taaaaagttg actttaaaaa      60
agtatcaata aatgtatgca tttctcacta gccttaaact ctgcatgaag tgtttgatga     120
```

-continued

```
gcagatgaag acaacatcat ttctagtttc agaaataata acagcatcaa aaccgcagct      180
gtaactccac tgagctcacg ttaagttttg atgtgtgaat atctgacaga actgacataa      240
tgagcactgc aaggatatca gacaagtcaa aatgaagaca gacaaaagta ttttttaata      300
taaaaatggt ctttatttct tcaatacaag gtaaactact attgcagttt aagaccaaca      360
caaaagttgg acagcaaatt gcttaacagt ctcctaaagg ctgaaaaaaa ggaacccatg      420
aaagctaaaa gttatgcagt atttcaagta taacatctaa aaatgatgaa acgatcccta      480
aaggtagaga ttaactaagt acttctgctg aaaatgtatt aaaatccgca gttgctagga      540
taccatctta ccttgttgag aaatacaggt ctccggcaac gcaacattca gcagactctt      600
tggcctgctg gaatcaggaa actgcttact atatacacat ataaatcctt tggagttggg      660
cattctgaga gacatccatt tcctgacatt ttgcagtgca actctgcatt ccaactcaga      720
caagctccca tgctgtattt caaagccatt tcttgaatag tttacccaga catccttgtg      780
caaattggga atgaggaaat gcaatggtac aggaagacaa tacagcctta tgtttagaaa      840
gtcagcagcg ctggtaatct tcataaaaat gtaactgttt tccaaatagg aatgtatttc      900
acttgtaaaa cacctggtcc ttttatatt acttttttt ttttttaagg acacctgcac      960
taatttgcaa tcacttgtat ttataaaagc acacgcactc ctcatttct tacatttgaa     1020
gatcagcaga atgtctcttt cataatgtaa taatcatatg cacagtttaa aatattttct     1080
attacaaaat acagtacaca agagggtgag gccaaagtct attacttgaa tatattccaa     1140
agtgtcagca ctgggggtgt aaaattacat tacatggtat gaataggcgg aattctttta     1200
caactgaaat gctcgatttc attgggatca aggtaagta ctgtttacta tcttcaagag     1260
acttcaatca agtcggtgta tttccaaaga agcttaaaag attgaagcac agacacaggc     1320
cacaccagag cctacacctg ctgcaataag tggtgctata gaaaggattc aggaactaac     1380
aagtgcataa tttacaaata gagatgcttt atcatacttt gcccaacatg ggaaaaaaga     1440
catcccatga gaatatccaa ctgaggaact tctctgtttc atagtaactc atctactact     1500
gctaagatgg tttgaaaagt acccagcagg tgagatatgt tcgggagtg gctgtgtggc     1560
agcgtgtccc aacacgacac aaagcacccc acccctatct gcaatgctca ctgcaaggca     1620
gtgccgtaaa cagctgcaac aggcatcact tctgcataaa tgctgtgact cgttagcatg     1680
ctgcaactgt gtttaaaacc tatgcactcc gttaccaaaa taatttaagt cccaaataaa     1740
tccatgcagc ttgcttccta tgccaacata ttttagaaag tattcattct tctttaagaa     1800
tatgcacgtg gatctacact tcctgggatc tgaagcgatt tatacctcag ttgcagaagc     1860
agtttagtgt cctggatctg ggaaggcagc agcaaacgtg cccgttttac atttgaaccc     1920
atgtgacaac ccgccttact gagcatcgct ctaggaaatt taaggctgta tccttacaac     1980
acaagaacca acgacagact gcatataaaa ttctataaat aaaaatagga gtgaagtctg     2040
tttgacctgt acacacagag catagagata aaaaaaaaag gaaatcagga attacgtatt     2100
tctataaatg ccatatattt ttactagaaa cacagatgac aagtatatac aacatgtaaa     2160
tccgaagtta tcaacatgtt aactaggaaa acatttacaa gcatttgggt atgcaactag     2220
atcatcaggt aaaaaatccc attagaaaaa tctaagcctc gccagtttca aggaaaaaa      2280
accagagaac gctcactact tcaaaggaaa aaaataaag catcaagctg gcctaaactt      2340
aataaggtat ctccatgtaac aacagctatc caagctttca agccacacta taaataaaaa     2400
cctcaagttc cgatcaacgt tttccataat gcaatcagaa ccaaaggcat tggcacagaa     2460
```

```
agcaaaaagg gaatgaaaga aaagggctgt acagtttcca aaaggttctt cttttgaaga    2520
aatgtttctg acctgtcaaa acatacagtc cagtagaaat tttactaaga aaaagaaca    2580 ccttacttaa aaaaaaaaaa caacaaaaaa aacaggcaaa aaaacctctc ctgtcactga    2640
gctgccacca cccaaccacc acctgctgtg ggctttgtct cccaagacaa aggacacaca    2700
gccttatcca atattcaaca ttacttataa aaacgctgat cagaagaaat accaagtatt    2760
tcctcagaga ctgttatatc ctttcatcgg caacaagaga tgaaatacaa cagagtgaat    2820
atcaaagaag gcggcaggag ccaccgtggc accatcaccg ggcagtgcag tgcccaactg    2880
ccgttttctg agcacgcata ggaagccgtc agtcacatgt aataaaccaa aacctggtac    2940
agttatatta tggatcc                                                  2957
```

```
<210> SEQ ID NO 2
<211> LENGTH: 660
<212> TYPE: DNA
<213> ORGANISM: Gallus gallus

<400> SEQUENCE: 2
gcgctgctga ctttctaaac ataaggctgt attgtcttcc tgtaccattg catttcctca     60
ttcccaattt gcacaaggat gtctgggtaa actattcaag aaatggcttt gaaatacagc    120
atgggagctt gtctgagttg gaatgcagag ttgcactgca aaatgtcagg aaatggatgt    180
ctctcagaat gcccaactcc aaaggattta tatgtgtata tagtaagcag tttcctgatt    240
ccagcaggcc aaagagtctg ctgaatgttg cgttgccgga gacctgtatt tctcaacaag    300
gtaagatggt atcctagcaa ctgcggattt taatacattt tcagcagaag tacttagtta    360
atctctacct ttagggatcg tttcatcatt tttagatgtt atacttgaaa tactgcataa    420
cttttagctt tcatgggttc cttttttttca gcctttagga gactgttaag caatttgctg    480
tccaactttt gtgttggtct taaactgcaa tagtagttta ccttgtattg aagaaataaa    540
gaccattttt atattaaaaa atactttgt ctgtcttcat tttgacttgt ctgatatcct    600
tgcagtgctc attatgtcag ttctgtcaga tattcacaca tcaaaactta acgtgagctc    660
```

```
<210> SEQ ID NO 3
<211> LENGTH: 449
<212> TYPE: DNA
<213> ORGANISM: Gallus gallus

<400> SEQUENCE: 3
aagcttcttt ggaaatacac cgacttgatt gaagtctctt gaagatagta aacagtactt     60
acctttgatc ccaatgaaat cgagcatttc agttgtaaaa gaattccgcc tattcatacc    120
atgtaatgta attttacacc cccagtgctg acactttgga atatattcaa gtaatagact    180
ttggcctcac cctcttgtgt actgtatttt gtaatagaaa atattttaaa ctgtgcatat    240
gattattaca ttatgaaaga gacattctgc tgatcttcaa atgtaagaaa atgaggagtg    300
cgtgtgcttt tataaataca agtgattgca aattagtgca ggtgtcctta aaaaaaaaa    360 aaagtaatat aaaaaggacc aggtgttta caagtgaaat acattcctat ttggaaaaca    420
gttacatttt tatgaagatt accagcgct                                     449
```

```
<210> SEQ ID NO 4
<211> LENGTH: 1668
<212> TYPE: DNA
<213> ORGANISM: Gallus gallus

<400> SEQUENCE: 4
```

```
ggatccataa tataactgta ccaggttttg gtttattaca tgtgactgac ggcttcctat        60
gcgtgctcag aaaacggcag ttgggcactg cactgcccgg tgatggtgcc acggtggctc       120
ctgccgcctt ctttgatatt cactctgttg tatttcatct cttgttgccg atgaaaggat       180
ataacagtct ctgaggaaat acttggtatt tcttctgatc agcgttttta taagtaatgt       240
tgaatattgg ataaggctgt gtgtcctttg tcttgggaga caaagcccac agcaggtggt       300
ggttgggtgg tggcagctca gtgacaggag aggttttttt gcctgttttt tttgttgttt       360
ttttttttta agtaaggtgt tcttttttct tagtaaaatt tctactggac tgtatgtttt       420
gacaggtcag aaacatttct tcaaaagaag aaccttttgg aaactgtaca gcccttttct       480
ttcattccct ttttgctttc tgtgccaatg cctttggttc tgattgcatt atggaaaacg       540
ttgatcggaa cttgaggttt ttatttatag tgtggcttga aagcttggat agctgttgtt       600
acatgagata ccttattaag tttaggccag cttgatgctt tattttttt cctttgaagt        660 agtgagcgtt ctctggtttt tttcctttga aactggcgag gcttagattt ttctaatggg       720 atttttacc tgatgatcta gttgcatacc caaatgcttg taaatgtttt cctagttaac        780
atgttgataa cttcggattt acatgttgta tatacttgtc atctgtgttt ctagtaaaaa       840
tatatggcat ttatagaaat acgtaattcc tgatttcctt ttttttttat ctctatgctc       900
tgtgtgtaca ggtcaaacag acttcactcc tattttt tat tatagaatt tatatgcagt       960 ctgtcgttgg ttcttgtgtt gtaaggatac agccttaaat ttcctagagc gatgctcagt      1020
aaggcgggtt gtcacatggg ttcaaatgta aaacgggcac gtttgctgct gccttcccag      1080
atccaggaca ctaaactgct tctgcaactg aggtataaat cgcttcagat cccaggaagt      1140
gtagatccac gtgcatattc ttaaagaaga atgaatactt tctaaaatat gttggcatag      1200
gaagcaagct gcatggattt atttgggact taaattattt tggtaacgga gtgcataggt      1260
tttaaacaca gttgcagcat gctaacgagt cacagcattt atgcagaagt gatgcctgtt      1320
gcagctgttt acggcactgc cttgcagtga gcattgcaga taggggtggg gtgctttgtg      1380
tcgtgttggg acacgctgcc acacagccac ctcccgaaca tatctcacct gctgggtact      1440
tttcaaacca tcttagcagt agtagatgag ttactatgaa acagagaagt tcctcagttg      1500
gatattctca tgggatgtct ttttttcccat gttgggcaaa gtatgataaa gcatctctat      1560
ttgtaaatta tgcacttgtt agttcctgaa tcctttctat agcaccactt attgcagcag      1620
gtgtaggctc tggtgtggcc tgtgtctgtg cttcaatctt ttaagctt                    1668
```

<210> SEQ ID NO 5
<211> LENGTH: 4672
<212> TYPE: DNA
<213> ORGANISM: Artificial Sequence
<220> FEATURE:
<223> OTHER INFORMATION: Description of Artificial Sequence: expression
    cloning vector

<400> SEQUENCE: 5

```
aggtcactgt gacctagatc cgcaggtcac tgtgacctac atctgatatc atcgtcgacg        60
gtatcgataa gcttcgaccg atccggcccc gcccagcgtc ttgtcattgg cgaattcgaa       120
cacgcagatg cagtcgggc ggcgcggtcc gaggtccact tcgcatatta aggtgacgcg        180
tgtggcctcg aacaccgagc gaccctgcag cgacccgctt aacagcgtca acagcgtgcc       240
gcagatctcg agagatctcg aggcatgcaa gcttggcatt ccggtactgt tggtaaaatg       300
gaagacgcca aaaacataaa gaaaggcccg gcgccattct atcctctaga ggatggaacc       360
```

```
gctggagagc aactgcataa ggctatgaag agatacgccc tggttcctgg aacaattgct    420
tttacagatg cacatatcga ggtgaacatc acgtacgcgg aatacttcga aatgtccgtt    480
cggttggcag aagctatgaa acgatatggg ctgaatacaa atcacagaat cgtcgtatgc    540
agtgaaaact ctcttcaatt ctttatgccg gtgttgggcg cgttatttat cggagttgca    600
gttgcgcccg cgaacgacat ttataatgaa cgtgaattgc tcaacagtat gaacatttcg    660
cagcctaccg tagtgtttgt ttccaaaaag gggttgcaaa aattttgaa cgtgcaaaaa     720 aaattaccaa taatccagaa aattattatc atggattcta aaacggatta ccagggattt    780
cagtcgatgt acacgttcgt cacatctcat ctacctcccg gttttaatga atacgatttt    840
gtaccagagt cctttgatcg tgacaaaaca attgcactga taatgaattc ctctggatct    900
actgggttac ctaagggtgt ggcccttccg catagaactg cctgcgtcag attctcgcat    960
gccagagatc ctattttggg caatcaaatc attccggata ctgcgatttt aagtgttgtt   1020
ccattccatc acgttttggg aatgtttact acactcggat atttgatatg tggatttcga   1080
gtcgtcttaa tgtatagatt tgaagaagag ctgtttttac gatcccttca ggattacaaa   1140
attcaaagtg cgttgctagt accaacccta ttttcattct tcgccaaaag cactctgatt   1200
gacaaatacg atttatctaa tttacacgaa attgcttctg gggggcgcacc tctttcgaaa   1260 gaagtcgggg aagcggttgc aaaacgcttc catcttccag ggatacgaca aggatatggg   1320
ctcactgaga ctacatcagc tattctgatt acacccgagg gggatgataa accgggcgcg   1380
gtcggtaaag ttgttccatt tttgaagcg aaggttgtgg atctggatac cgggaaaacg   1440
ctgggcgtta atcagagagg cgaattatgt gtcagaggac ctatgattat gtccggttat   1500
gtaaacaatc cggaagcgac caacgccttg attgacaagg atggatggct acattctgga   1560
gacatagctt actgggacga agacgaacac ttcttcatag ttgaccgctt gaagtcttta   1620
attaaataca aaggatatca ggtggccccc gctgaattgg aatcgatatt gttacaacac   1680
cccaacatct tcgacgcggg cgtggcaggt cttcccgacg atgacgccgg tgaacttccc   1740
gccgccgttg ttgttttgga gcacggaaag acgatgacgg aaaaagagat cgtggattac   1800
gtggccagtc aagtaacaac cgcgaaaaag ttgcgcggag gagttgtgtt tgtggacgaa   1860
gtaccgaaag tcttaccgg aaaactcgac gcaagaaaaa tcagagagat cctcataaag   1920
gccaagaagg gcggaaagtc caaattgtaa aatgtaactg tattcagcga tgacgaaatt   1980
cttagctatt gtaatactgc gatgagtggc agggcgggc gtaatttttt taaggcagtt   2040
attggtgccc ttaaacgcct ggtgctacgc ctgaataagt gataataagc ggatgaatgg   2100
cagaaattcg ccggatcttt gtgaaggaac cttacttctg tggtgtgaca taattggaca   2160
aactacctac agagatttaa agctctaagg taaatataaa atttttaagt gtataatgtg   2220
ttaaactact gattctaatt gtttgtgtat tttagattcc aacctatgga actgatgaat   2280
gggagcagtg gtggaatgcc tttaatgagg aaaacctgtt ttgctcagaa gaaatgccat   2340
ctagtgatga tgaggctact gctgactctc aacattctac tcctccaaaa agaagagaa    2400 aggtagaaga ccccaaggac tttccttcag aattgctaag ttttttgagt catgctgtgt   2460
ttagtaatag aactcttgct tgctttgcta tttacaccac aaaggaaaaa gctgcactgc   2520
tatacaagaa aattatggaa aaatattctg taaccttat aagtaggcat aacagttata   2580
atcataacat actgttttt cttactccac acaggcatag agtgtctgct attaataact   2640
atgctcaaaa attgtgtacc tttagctttt taatttgtaa aggggttaat aaggaatatt   2700
```

-continued

```
tgatgtatag tgccttgact agagatcata atcagccata ccacatttgt agaggtttta    2760
cttgctttaa aaacctccc acacctcccc ctgaacctga acataaaat gaatgcaatt     2820 gttgttgtta acttgtttat tgcagcttat aatggttaca aataaagcaa tagcatcaca    2880
aatttcacaa ataaagcatt tttttcactg cattctagtt gtggtttgtc caaactcatc    2940
aatgtatctt atcatgtctg gatccgtcga gggggatcca ctagttctag agcggccgcc    3000
accgggatcc ataatataac tgtaccaggt tttggtttat tacatgtgac tgacggcttc    3060
ctatgcgtgc tcagaaaacg gcagttgggc actgcactgc ccggtgatgg tgccacggtg    3120
gctcctgccg ccttctttga tattcactct gttgtatttc atctcttgtt gccgatgaaa    3180
ggatataaca gtctctgagg aaatacttgg tatttcttct gatcagcgtt tttataagta    3240
atgttgaata ttggataagg ctgtgtgtcc tttgtcttgg gagacaaagc ccacagcagg    3300
tggtggttgg gtggtggcag ctcagtgaca ggagaggttt ttttgcctgt ttttttttgtt    3360 gtttttttt tttaagtaag gtgttctttt ttccttagtaa aatttctact ggactgtatg    3420
ttttgacagg tcagaaacat ttcttcaaaa gaagaacctt ttggaaactg tacagcccctt    3480 ttctttcatt ccctttttgc tttctgtgcc aatgcctttg gttctgattg cattatggaa    3540
aacgttgatc ggaacttgag gttttttattt atagtgtggc ttgaaagctt ggatagctgt    3600
tgttacatga gataccttat taagtttagg ccagcttgat gctttatttt ttttcctttg    3660
aagtagtgag cgttctctgg ttttttttcct ttgaaactgg cgaggcttag atttttctaa    3720 tgggatttt tacctgatga tctagttgca tacccaaatg cttgtaaatg ttttcctagt    3780
taacatgttg ataacttcgg atttacatgt tgtatatact tgtcatctgt gtttctagta    3840
aaaatatatg gcatttatag aaatacgtaa ttcctgattt cctttttttt ttatctctat    3900
gctctgtgtg tacaggtcaa acagacttca ctcctatttt tatttataga atttatatg    3960 cagtctgtcg ttggttcttg tgttgtaagg atacagcctt aaatttccta gagcgatgct    4020
cagtaaggcg ggttgtcaca tgggttcaaa tgtaaaacgg gcacgtttgc tgctgccttc    4080
ccagatccag gacactaaac tgcttctgca actgaggtat aaatcgcttc agatcccagg    4140
aagtgtagat ccacgtgcat attcttaaag aagaatgaat actttctaaa atatgttggc    4200
ataggaagca agctgcatgg atttatttgg gacttaaatt attttggtaa cggagtgcat    4260 aggtttaaa cacagttgca gcatgctaac gagtcacagc atttatgcag aagtgatgcc    4320
tgttgcagct gtttacggca ctgccttgca gtgagcattg cagatagggg tgggtgctt    4380 tgtgtcgtgt tgggacacgc tgccacacag ccacctcccg aacatatctc acctgctggg    4440
tacttttcaa accatcttag cagtagtaga tgagttacta tgaaacagag aagttcctca    4500
gttggatatt ctcatgggat gtctttttttc ccatgttggg caaagtatga taaagcatct    4560
ctatttgtaa attatgcact tgttagttcc tgaatccttt ctatagcacc acttattgca    4620
gcaggtgtag gctctggtgt ggcctgtgtc tgtgcttcaa tctttaagc tt           4672
```

<210> SEQ ID NO 6
<211> LENGTH: 401
<212> TYPE: DNA
<213> ORGANISM: Gallus gallus

<400> SEQUENCE: 6

```
gatctgcaaa ttgcttaaca gtctcctaaa ggctgaaaaa aaggaaccca tgaaagctaa     60
aagttatgca gtatttcaag tataacatct aaaaatgatg aaacgatccc taaaggtaga   120
gattaactaa gtacttctgc tgaaaatgta ttaaaatccg cagttgctag gataccatct   180
```

-continued

```
taccttgttg agaaatacag gtctccggca acgcaacatt cagcagactc tttggcctgc      240
tggaatcagg aaactgctta ctatatacac atataaaatc ctttggagtt gggcattctg      300
agagacatcc atttcctgac attttgcagt gcaactctgc attccaactc agacaagctc      360
ccatgctgta tttcaaagcc atttcttgaa tagtttggat c                          401
```

<210> SEQ ID NO 7
<211> LENGTH: 392
<212> TYPE: DNA
<213> ORGANISM: Gallus gallus

<400> SEQUENCE: 7

```
gatctaagtc agcagcgctg gtaatcttca taaaaatgta actgttttcc aaataggaat       60
gtatttcact tgtaaaacac ctggtccttt ttatattact tttttttttt tttaaggaca      120
cctgcactaa tttgcaatca cttgtattta taaaagcaca cgcactcctc attttcttac      180
atttgaagat cagcagaatg tctctttcat aatgtaataa tcatatgcac agtttaaaat      240
attttctatt acaaaataca gtacacaaga gggtgaggcc aaagtctatt acttgaatat      300
attccaaagt gtcagcactg ggggtgtaaa attacattac atggtatgaa taggcggaat      360
tcttttacaa ctgaaatgct cgatttcgga tc                                    392
```

<210> SEQ ID NO 8
<211> LENGTH: 464
<212> TYPE: DNA
<213> ORGANISM: Gallus gallus

<400> SEQUENCE: 8

```
gatctacaac acaagaacca acgacagact gcatataaaa ttctataaat aaaaatagga       60
gtgaagtctg tttgacctgt acacacagag catagagata aaaaaaaaag gaaatcagga      120
attacgtatt tctataaatg ccatatattt ttactgaaaa cacagatgac aagtatatac      180
aacatgtaaa tccgaagtta tcaacatgtt aactaggaaa acatttacaa gcatttgggt      240
atgcaactag atcatcaggt aaaaaatccc attagaaaaa tctaagcctc gccagtttca      300
aaggaaaaaa accagagaac gctcactact tcaaggaaaa aaaataaag catcaagctg       360 gcctaaactt aataaggtat tcatgtaacc aacagctatc caagctttca agccacacta      420
taaataaaaa cctcaagttc cgatcaacgt tggatcccgg gatc                       464
```

<210> SEQ ID NO 9
<211> LENGTH: 431
<212> TYPE: DNA
<213> ORGANISM: Gallus gallus

<400> SEQUENCE: 9

```
gatctgggct gtacagtttc caaaaggttc ttcttttgaa gaaatgtttc tgacctgtca       60
aaacatacag tccagtagaa attttactaa gaaaaagaa caccttactt aaaaaaaaaa      120
aacaacaaaa aaaacaggca aaaaaacctc tcctgtcact gagctgccac cacccaacca     180
ccacctgctg tgggctttgt ctcccaagac aaaggacaca cagccttatc caatattcaa      240
cattacttat aaaaacgctg atcagaagaa ataccaagta tttcctcaga gactgttata      300
tcctttcatc ggcaacaaga gatgaaatac aacagagtga atatcaaaga aggcggcagg      360
agccaccgtg gcaccatcac cgggcagtgc agtgcccaac tgccgttttc tgagcacgca      420
taggaaggat c                                                           431
```

MATRIX ATTACHMENT REGIONS AND METHODS FOR USE THEREOF

RELATED APPLICATIONS

This application claims the benefit of U.S. Ser. No. 60/264,355, filed Jan. 26, 2001 and U.S. Ser. No. 60/281,391, filed Apr. 4, 2001, both of which are incorporated herein by reference in their entireties.

FIELD OF THE INVENTION

The present invention relates generally to matrix attachment regions (MARs) and to methods for use of MARs. In particular, the invention relates to the uses of such methods for the development of stable eukaryotic cell lines.

BACKGROUND OF THE INVENTION

Eukaryotic cell lines can be genetically modified to express one or more desired proteins. Current selection and screening procedures to identify a clonal cell line with the requisite expression characteristics for regulated expression or production are tedious and time-consuming. For example, in Chinese hamster ovary (CHO) cells, the classical approach to achieve maximal expression involves the use of mutant cell lines and a gradual increase in the selection pressure over several months for a co-transfected selection marker such as dihydrofolate reductase. (Kaufman and Sharp, 1982; Schimke et al., 1982) While new approaches to the problem include the identification of rare sites on a chromosome with high transcriptional activity, combined with targeted integration and the improvement of selection and of screening procedures (Fussenegger et al., 1999), these are nevertheless all labor-intensive processes.

SUMMARY OF THE INVENTION

In one aspect, the present invention involves a method for transforming eukaryotic cells using transfection of two or more unlinked nucleic acid vectors, the first vector having a promoter and a heterologous gene coding for a desired protein, and the second vector having at least one chromatin element. In preferred embodiments, the chromatin element is a MAR element (e.g., a chicken lysozyme MAR element). In alternative embodiments of the present invention, the nucleic acid vectors are incorporated into the eukaryotic cell chromatin or remain episomal.

In another aspect, the present invention involves a method for transforming eukaryotic cells using transfection of two or more unlinked nucleic acid vectors, the first vector having a promoter and a heterologous gene coding for a desired protein, and the second vector having at least one chromatin element, and contacting the transfected cells with butyrate.

In yet another aspect, the present invention provides a method for transforming eukaryotic cells using transfection of two or more unlinked nucleic acid vectors, the first vector having a promoter, a heterologous gene coding for a desired protein and a first chromatin element; and the second vector having a second chromatin element. In alternative embodiments, the first chromatin element may be located 5' (upstream) or 3' (downstream) of the promoter and the heterologous gene. In other embodiments, the second vector contains two or more chromatin elements (e.g., a third, fourth, fifth or six chromatin element). In preferred embodiments of the present invention, at least one of the first, second, third, fourth, fifth and sixth chromatin elements may be MAR elements (e.g., a chicken lysozyme MAR element). In another preferred embodiment, the eukaryotic cell is co-transfected with a third vector. This third vector may include at least one genes (e.g. structural, regulatory or selection genes) and/or at least one chromatin element (e.g., a MAR element). In certain preferred embodiments of the present invention, the molar ratios of the first, second, and possibly third vectors are modulated.

In a further aspect, the present invention provides a method of selecting a eukaryotic cell expressing a gene encoding a recombinant proteins by transfecting a first eukaryotic cell with a first vector having a first promoter and a first gene, and a second vector having a MAR element and transfecting a second eukaryotic cell with the first vector having the first promoter and the first gene, measuring and comparing the expression of the gene in the first and second eukaryotic cell, and selecting the first eukaryotic cell if the expression of the first gene is greater in the first eukaryotic cell than in the second eukaryotic cell.

In another aspect, the present invention provides compositions of one or more nucleic acid vectors. In one embodiment, the invention provides a composition of two nucleic acid vectors, the first vector having a promoter and a heterologous gene coding for a desired protein, and the second vector having a MAR element. In other embodiments, the composition further comprises butyrate.

In another aspect, the present invention provides one or more eukaryotic cells containing two or more nucleic acid vectors, the first vector having a promoter and a heterologous gene coding for a desired protein, and the second vector having a MAR element. In an embodiment, the invention provides one or more eukaryotic cells containing two or more nucleic acid vectors, the first vector having a promoter, a heterologous gene coding for a desired protein and a MAR element, and the second vector having at least one MAR element. In some embodiments, the one or more eukaryotic cells are butyrate-treated cells.

In a further aspect, the present invention provides kits, containing in one or more containers, two or more nucleic acid vectors, the first vector having a promoter and a heterologous gene coding for a desired protein, and the second vector having a MAR element, and directions for use thereof. In an embodiment, the invention provides kits, containing in one or more containers, one or more eukaryotic cells containing two or more nucleic acid vectors, the first vector having a promoter, a heterologous gene coding for a desired protein and a MAR element, and the second vector having at least one MAR element. In an embodiment, the kit additionally comprises butyrate.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and are not intended to be limiting.

Other features and advantages of the invention will be apparent from the following detailed description and from the claims.

BRIEF DESCRIPTION OF THE DRAWINGS

FIG. 3 demonstrates gene expression in stable CHO clones.

FIG. 4 shows the regulated gene expression in stable C2C12 clones. FIG. 4B shows the expression in clones selected by FACS with the stably integrated regulated expression system. The β-galactosidase activity, normalized with respect to protein content, is shown for 10 clones. White columns correspond to expression in the absence of doxycycline (no dox); black columns correspond to expression induced by the addition of doxycycline (dox), with the fold induction indicated above the black column.

In FIG. 6A, cells were transfected with 1.69 μg of control (first two rows of columns) or with equimolar amount (2.28 μg) of MAR-containing plasmids (rows 3 and 4) per three wells. The ratio between the heavy and light chain-encoding plasmids was 2:1. The total amount of plasmid DNA was adjusted to 2.5 μg with pGL3 (Promega, Inc). Rows 2 and 4 result from cell treated by the addition of 10 mM sodium butyrate in the culture medium. In FIG. 6B cells were transfected with 2.47 μg of control (first two rows of columns) or with equimolar amount (3.27 μg) of MAR-containing plasmids (rows 3 and 4) per three wells, respectively. The ratio between the heavy and light chain-encoding plasmids was 2:1. Rows 2 and 4 result from cell treated by the addition of 10 mM sodium butyrate in the culture medium.

FIG. 7. demonstrates the effect of MAR fragments on a reporter luciferase gene in stably transfected CHO cells.

DETAILED DESCRIPTION OF THE INVENTION

Figure 1:
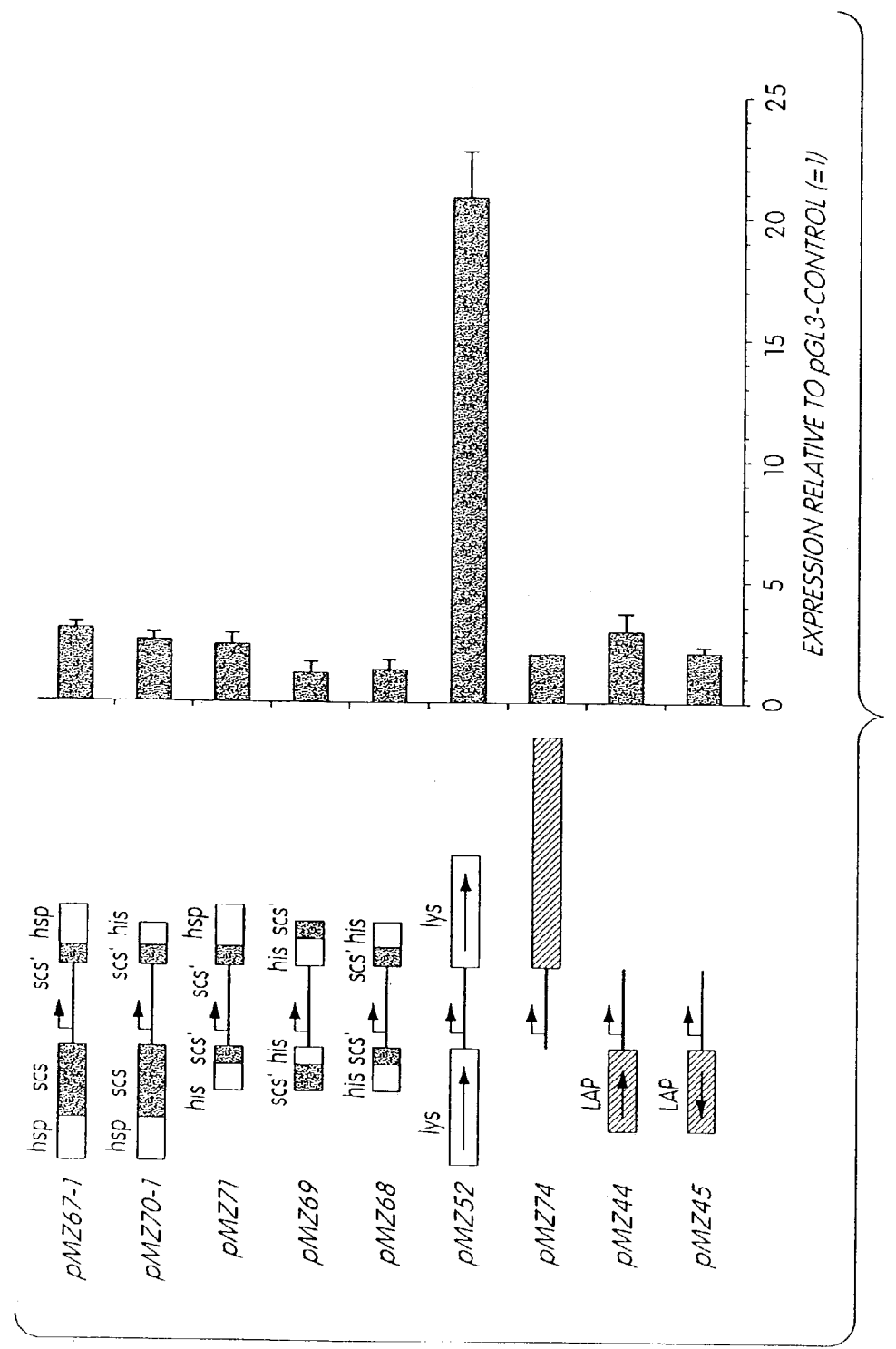
FIG. 1 demonstrates the effect of chromatin elements on stable transgene expression. Chromatin elements were cloned on one or both sides of the luciferase expression unit (black line and arrow) of the pGL3-Control plasmid. The resulting constructs, shown schematically in the left hand panel, were digested with PvuI and co-transfected with pSV2neo. The luciferase activity of pools of CHO clones, normalized with respect to protein content and expressed relative to pGL3-Control, is shown in the right hand panel. Error bars correspond to the standard error, based on at least three independent transfections. Chromatin elements examined include those chromatin elements potentially capable of overcoming position effects, including boundary elements (BEs; black boxes), matrix attachment regions (MARs; white boxes), and locus control regions (LCRs; hatched boxes). The arrow depicting lys MAR orientation points from BamHI to XbaI, while the arrow for the LAP LCR points in the direction of the LAP gene and its direction of transcription.

To date, the development of stable cell lines has been hampered by the negative effects of surrounding chromatin on the expression of randomly integrated vector sequences. Chromatin elements, such as boundary elements, matrix attachment regions, and locus control regions, are known to exert an effect on gene expression only when integrated in the genome. While the use of chromatin elements in the next generation of gene therapy vectors is currently being considered to improve expression of therapeutic transgenes (Neff et al., 1997), few studies have systematically addressed the potential of such elements to modify or improve the expression of gene constructs. In order to exploit the favorable properties of chromatin elements in the development of stable cell lines, their usefulness must be established. The elements used to this end should improve the frequency of obtaining high-level expression clones, irrespective of the chromosomal integration site and the number of copies integrated. This effect should not be specific to a particular cell type, but rather should be observed in all cell lines commonly used in biotechnology and gene or cell therapy. Furthermore, the element should act independently of the promoter, enabling it to be used with diverse constructs.

The compositions and methods according to the present invention possess new capacities and abilities in the transfection of eukaryotic cells. The present invention enables the transfection of nucleic acids, such as genes encoding recombinant proteins, into eukaryotic cells, particularly mammalian cells.

The compositions and methods according to the present invention are particularly suited for generating cell lines that express one or more genes encoding for recombinant proteins.

Variability in expression levels of a heterologous gene transfected into a eukaryotic cell is thought to reflect the influence of the chromatin structure and/or the presence of regulatory elements at the site of integration of the heterologous gene in the host genome, a phenomenon referred to as the "position effect". A simple and rapid approach to overcome position effects is to make use of chromatin elements that prevent the neighboring chromatin from affecting transgene expression. This approach improves the probability of isolating a clone exhibiting the desired regulated expression. This approach is useful, e.g., for ex vivo gene therapy, or for high-level expression for production of a recombinant protein, thereby reducing the time spent screening clones. Furthermore, position-independent transgene expression has significant potential in the construction of regulated gene expression systems, because the expression of a therapeutic gene (along with its controlling components) would be independent of the chromatin structure at the integration site. Chromatin elements that are potentially capable of overcoming position effects, and hence are of interest for the development of stable cell lines, include boundary elements (BEs), matrix attachment regions (MARs), locus control regions (LCRs), and universal chromatin opening elements (UCOEs).

Boundary elements ("BEs"), or insulator elements, define boundaries in chromatin in many cases (Bell and Felsenfeld, 1999; Udvardy, 1999) and may play a role in defining a transcriptional domain in vivo. BEs lack intrinsic promoter/enhancer activity, but rather are thought to protect genes from the transcriptional influence of regulatory elements in the surrounding chromatin. The enhancer-block assay is commonly used to identify insulator elements. In this assay, the chromatin element is placed between an enhancer and a promoter, and enhancer-activated transcription is measured. Boundary elements have been shown to be able to protect stably transfected reporter genes against position effects in *Drosophila*, yeast and in mammalian cells (Bi and Broach, 1999; Cuvier et al., 1998; Walters et al., 1999). They have also been shown to increase the proportion of transgenic mice with inducible transgene expression (Wang et al., 1997).

Matrix Attachment Regions ("MARs"; also known as Scaffold Attachment Regions or Scaffold/Matrix Attachment Regions ("S/MARs")) are DNA sequences that bind isolated nuclear scaffolds or nuclear matrices in vitro with high affinity (Hart and Laemmli, 1998). As such, they may define boundaries of independent chromatin domains, such that only the encompassing cis-regulatory elements control the expression of the genes within the domain. However, their ability to fully shield a chromosomal locus from nearby chromatin elements, and thus confer position-independent gene expression, has not been seen in stably transfected cells (Poljak et al., 1994). On the other hand, MAR sequences have been shown to interact with enhancers to increase local chromatin accessibility (Jenuwein et al., 1997). Specifically, MAR elements can enhance expression of heterologous genes in cell culture lines (Kalos and Fournier, 1995; Klehr et al., 1991; Phi-Van et al., 1990; Poljak et al., 1994), transgenic mice (Castilla et al., 1998) and plants (Allen et al., 1996). The utility of MAR sequences for developing improved vectors for gene therapy is also recognized (Agarwal et al., 1998).

Locus control regions ("LCRs") are cis-regulatory elements required for the initial chromatin activation of a locus and subsequent gene transcription in their native locations (reviewed in Grosveld, 1999). The activating function of LCRs also allows the expression of a coupled transgene in the appropriate tissue in transgenic mice, irrespective of the site of integration in the host genome. While LCRs generally confer tissue-specific levels of expression on linked genes, efficient expression in nearly all tissues in transgenic mice has been reported for a truncated human T-cell receptor LCR (Ortiz et al., 1997) and a rat LAP LCR (Talbot et al., 1994). The most extensively characterized LCR is that of the globin locus. Its use in vectors for the gene therapy of sickle cell disease and β-thalassemias is currently being evaluated (Pawliuk et al., 1998).

Ubiquitous chromatin opening elements ("UCOEs", also known as "ubiquitously-acting chromatin opening elements") have recently been reported (See WO00/05393).

The chicken lysozyme 5' MAR element is able to significantly improve stable transgene expression in CHO cells, a cell line commonly used in recombinant protein production. The chicken lysozyme 5' MAR element is also able to significantly improve transient transfections, particularly when the transfected cells are contacted with butyrate. This chicken MAR element has previously been shown to enhance transcription from a heterologous promoter in heterologous cells (Phi-Van et al., 1990), and to confer position-independent hormonal and developmental regulation of the expression of the whey acidic protein gene in transgenic mice (McKnight et al., 1992).

Importantly, co-transfection of a plasmid bearing the chicken lysozyme 5' MAR element with one or more expression vectors results in increased stable transgene expression. This simple approach obviates the necessity of cloning MAR elements in expression constructs. Furthermore, the size of the MAR element is no longer a limitation. Co-transfection with the MAR element is shown to increase the average level of expression of stable clones, as well as to increase the probability of obtaining clones expressing at higher levels than those obtained upon transfection of the expression plasmids alone.

Without wishing to be bound by theory, it is possible that the distance and sequence between the MAR elements and the expression unit is an important consideration. The effect of MARs has been detected for a proximal gene, and not for a more distally located one (Bode et al., 1995). The effect of co-transfection of the MAR has not found to be saturated (See FIG. 2), a potential limitation of this technique is the quantity of DNA that can be transfected per cell. One skilled in the art would be able to determine the maximum quantity of DNA to transfect for a given cell type with minimal experimentation.

As used herein, the following definitions are supplied in order to facilitate the understanding of this case. To the extent that the definitions vary from meanings circulating within the art, the definitions below are to control.

"Chromatin" is the nucleic acid material having the chromosomes of a eukaryotic cell, and refers to DNA, RNA and associated proteins.

A "chromatin element" means a nucleic acid sequence on a chromosome.

"Cis" refers to the placement of two or more elements (such as chromatin elements) on the same nucleic acid molecule (such as the same vector or chromosome).

"Trans" refers to the placement of two or more elements (such as chromatin elements) on two or more different nucleic acid molecules (such as on two vectors or two chromosomes).

"Cis activation" refers to activation of a gene by an activator (such as an enhancer) located on the same nucleic acid molecule (such as the same vector or chromosome).

"Downstream" refers to the direction going towards the 3' end of a nucleotide sequence.

An "enhancer" is a nucleotide sequence that acts to potentiate the transcription of genes independent of the identity of the gene, the position of the sequence in relation to the gene, or the orientation of the sequence. The vectors of the present invention optionally include enhancers.

A "gene" is a deoxyribonucleotide (DNA) sequence coding for a given mature protein. As used herein, the term "gene" shall not include untranslated flanking regions such as RNA transcription initiation signals, polyadenylation addition sites, promoters or enhancers.

A "selection gene" is a gene that confers a phenotype on cells which express the gene as a detectable protein. Examples of selection genes include, but are not limited to, antibiotic resistance genes and genes encoding enzymes that produce or modify intermediate compounds of cellular metabolism or compounds exogenously added to the cell (e.g. drugs).

A "selection agent" is a condition, agent or substance that enables the detection of the expression of a selection gene.

"Phenotype" refers to the observable properties of a cell as expressed by the cellular genotype.

A "product gene" is a gene that encodes a protein product having desirable characteristics such as diagnostic or therapeutic utility. A product gene includes, e.g., structural genes and regulatory genes.

A "structural gene" refers to a gene that encodes a structural protein. Examples of structural genes include but are not limited to, cytoskeletal proteins, extracellular matrix proteins, enzymes, nuclear pore proteins and nuclear scaffold proteins, ion channels and transporters, contractile proteins, and chaperones. Preferred structural genes encode for antibodies or antibody fragments.

A "regulatory gene" refers to a gene that encodes a regulatory protein. Examples of regulatory proteins include, but are not limited to, transcription factors, hormones, growth factors, cytokines, signal transduction molecules, oncogenes, proto-oncogenes, transmembrane receptors, and protein kinases.

"Genotype" refers to the genetic information contained within a cell as opposed to its expression, which is observed as the cellular phenotype.

"Ligation" is the process for forming a phosphodiester bond between the 5' and 3' ends of two DNA strands. This may be accomplished by several well known enzymatic techniques, including, but not limited to, blunt end ligation by T4 DNA ligase.

"Orientation" refers to the order of nucleotides in a given DNA sequence. For example, an inverted orientation of a DNA sequence is one in which the 5' to 3' order of the sequence in relation to another sequence is reversed when compared to a point of reference in the DNA from which the sequence was obtained. Such reference points can include the direction of transcription of other specified DNA sequences in the source DNA and/or the origin of replication of replicable vectors containing the sequence.

"Transcription" means the synthesis of RNA from a DNA template.

"Translation" refers to the synthesis of a polypeptide from messenger RNA.

The term "vector" as used herein refers to a nucleic acid molecule capable of transporting another nucleic acid to which it has been linked.

"Eukaryotic cell" refers to any mammalian or non-mammalian cell from a eukaryotic organism. By way of non-limiting example, any eukaryotic cell which is capable of being maintained under cell culture conditions and subsequently transfected would be included in this invention. Especially preferable cell types include, e.g. stem cells, embryonic stem cells, Chinese hamster ovary cells (CHO), COS, BHK21, NIH3T3, HeLa, C2C12, cancer cells, and primary differentiated or undifferentiated cells. Other suitable host cells are known to those skilled in the art.

"Transformation" as used herein refers to modifying a eukaryotic cell by the addition of a nucleic acid. For example, transforming a cell could include transfecting the cell with a nucleic acid, such as a DNA vector.

"Transfection" is the introduction of a nucleic acid into a recipient eukaryotic cell, such as by electroporation or by chemical means. Transfection may be detected in some cases by an alteration in cell phenotype. In some cases, transfected cells are called transfectants and pre-transfection cells are referred to as parental cells.

"Promoter" as used herein refers to a nucleic acid sequence that regulates expression of a gene.

"Co-transfection" means the process of transfecting a eukaryotic cell with more than one exogenous gene foreign to the cell, one of which may confer a selectable phenotype on the cell.

Eukaryotic transfection of nucleic acid vectors is, in general, a well-known process, and may be accomplished by a variety of standard methods. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". In general, expression vectors of utility in recombinant DNA techniques are often in the form of plasmids. As used herein, "plasmid" and "vector" are used interchangeably, as the plasmid is the most commonly used vector form. However, the invention is intended to include such other forms of expression vectors, including, but not limited to, viral vectors (e.g., replication defective retroviruses, adenoviruses and adeno-associated viruses), which serve equivalent functions.

The recombinant expression vectors of the invention contain a nucleic acid of the invention in a form suitable for expression of the nucleic acid in a host cell. Specifically, this means that the recombinant expression vectors include one or more regulatory sequences, selected on the basis of the host cells to be used for expression, that is operatively-linked to the nucleic acid sequence to be expressed. Within a recombinant expression vector, the term "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). Such regulatory sequences are described, for example, in Goeddel, GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transfected, the level of expression of protein desired, etc.

The recombinant expression vector(s) used herein can be designed for expression of desired proteins in eukaryotic cells. Suitable host cells are discussed further in Goeddel, GENE EXPRESSION TECHNOLOGY: METHODS IN ENZYMOLOGY 185, Academic Press, San Diego, Calif. (1990).

The expression vector(s) used herein may be a yeast expression vector. Examples of vectors for expression in yeast *Saccharomyces cerivisae* include pYepSec1 (Baldari, et al., 1987. *EMBO J.* 6: 229–234), pMFa (Kurjan and Herskowitz, 1982. *Cell* 30: 933–943), pJRY88 (Schultz et al., 1987. *Gene* 54: 113–123), pYES2 (Invitrogen Corporation, San Diego, Calif.), and picZ (InVitrogen Corp, San Diego, Calif.).

Alternatively, the expression vector(s) used herein may be a baculovirus expression vector. Baculovirus vectors available for expression of proteins in cultured insect cells (e.g., SF9 cells) include the pAc series (Smith, et al., 1983. *Mol. Cell. Biol.* 3: 2156–2165) and the pVL series (Lucklow and Summers, 1989. *Virology* 170: 31–39).

A nucleic acid of the invention may also be expressed in mammalian cells using a mammalian expression vector. Examples of mammalian expression vectors include pCDM8 (Seed, 1987. *Nature* 329: 840) and pMT2PC (Kaufman, et al., 1987. *EMBO J.* 6: 187–195). When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

A recombinant mammalian expression vector is capable of directing expression of the nucleic acid preferentially in a particular cell type (e.g. tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. *Genes Dev.* 1: 268–277), lymphoid-specific promoters (Calame and Eaton, 1988. *Adv. Immunol.* 43: 235–275), in particular promoters of T cell receptors (Winoto and Baltimore, 1989. *EMBO J.* 8: 729–733) and immunoglobulins (Banerji, et al., 1983. *Cell* 33: 729–740; Queen and Baltimore, 1983. *Cell* 33: 741–748), neuron-specific promoters (e.g., the neurofilament promoter; Byrne and Ruddle, 1989. *Proc. Natl. Acad. Sci. USA* 86: 5473–5477), pancreas-specific promoters (Edlund, et al., 1985. *Science* 230: 912–916), and mammary gland-specific promoters (e.g., milk whey promoter; U.S. Pat. No. 4,873,316 and European Application Publication No. 264,166). Developmentally-regulated promoters are also encompassed. Examples of such promoters include, e.g., the murine hox promoters (Kessel and Gruss, 1990. *Science* 249: 374–379) and the α-fetoprotein promoter (Campes and Tilghman, 1989. *Genes Dev.* 3: 537–546).

Regulatable gene expression promoters are well known in the art, and include, by way of non-limiting example, any promoter that modulates expression of a gene encoding a desired protein by binding an exogenous molecule, such as the CRE/LOX system, the TET system, the NFkappaB/UV light system, the Leu3p/isopropylmalate system, and the GLVPc/GAL4 system (See e.g., Sauer, 1998, Methods 14(4): 381–92; Lewandoski, 2001, Nat. Rev. Genet 2(10): 743–55; Legrand-Poels et al., 1998, J. Photochem. Photobiol. B. 45:1–8; Guo et al., 1996, FEBS Lett. 390(2):191–5; Wang et al., PNAS USA, 1999, 96(15):8483–8).

Moreover, the terms "host cell" and "recombinant host cell" are used interchangeably herein to indicate a eukaryotic cell into which one or more vectors of the invention have been introduced. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

As noted, the term "transfection" refers to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these successful integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding a structural or regulatory protein, or can be introduced on a separate vector. Cells stably transfected with the introduced nucleic acid can be identified by drug selection (e.g., cells that have incorporated the selectable marker gene will survive, while the other cells die).

The present invention involves compositions and methods that can modulate the efficiency of eukaryotic cell transfection using chromatin elements (e.g., MAR elements, BEs and LCRs). In accordance with the invention, MAR elements may be used in eukaryotic cell transfection methods. For example, a MAR element suitable for use in the present invention includes chicken lysozyme MAR element, which is shown in SEQ ID NO: 1 (See Table 1A) or a fragment thereof. Also useful are the nucleotide sequences recited in GenBank Accession numbers X52989 (SEQ ID NO: 2), X84223 (SEQ ID NO: 3), X98408 (SEQ ID NO: 4), and AJ277960 (SEQ ID NO: 5) (See Tables 1B–1E) or fragments thereof. Additional MAR elements to be used in accordance with the invention may be identified, isolated, and cloned using a variety of techniques well known to those of ordinary skill in the art.

TABLE 1A

MAR Element (SEQ ID NO:1)
tctagaaaacaatatatttccaaatgaaaaaaaaatctgataaaaagttg actttaaaaaagtatcaataaatgtatgcatttctcactagccttaaact ctgcatgaagtgtttgatgagcagatgaagacaacatcatttctagtttc agaaataataacagcatcaaaaccgcagctgtaactccactgagctcacg ttaagttttgatgtgtgaatatctgacagaactgacataatgagcactgc aaggatatcagacaagtcaaaatgaagacagacaaaagtattttttaata taaaaatggtctttatttcttcaatacaaggtaaactactattgcagttt aagaccaacacaaaagttggacagcaaattgcttaacagtctcctaaagg ctgaaaaaaggaacccatgaaagctaaaagttatgcagtatttcaagta taacatctaaaaatgatgaaacgatccctaaaggtagagattaactaagt acttctgctgaaaatgtattaaaatccgcagttgctaggataccatctta ccttgttgagaaatacaggtctccggcaacgcaacattcagcagactctt tggcctgctggaatcaggaaactgcttactatatacacatataaatcctt tggagttgggcattctgagagacatccatttcctgacattttgcagtgca actctgcattccaactcagacaagctcccatgctgtatttcaaagccatt tcttgaatagtttacccagacatccttgtgcaaattgggaatgaggaaat gcaatggtacaggaagacaatacagccttatgtttagaaagtcagcagcg ctggtaatcttcataaaaatgtaactgttttccaaataggaatgtatttc acttgtaaaacacctggtccttttttatattactttttttttttttaagg acacctgcactaatttgcaatcacttgtatttataaaagcacacgcactc ctcattttcttacatttgaagatcagcagaatgtctctttcataatgtaa taatcatatgcacagtttaaaatattttctattacaaaatacagtacaca agagggtgaggccaaagtctattacttgaatatattccaaagtgtcagca ctgggggtgtaaaattacattacatggtatgaataggcggaattcttta TABLE 1A-continued MAR Element caactgaaatgctcgatttcattgggatcaaaggtaagtactgtttacta tcttcaagagacttcaatcaagtcggtgtatttccaaagaagcttaaaag attgaagcacagacacaggccacaccagagcctacacctgctgcaataag tggtgctatagaaaggattcaggaactaacaagtgcataatttacaaata gagatgctttatcatactttgcccaacatgggaaaaaagacatcccatga gaatatccaactgaggaacttctctgtttcatagtaactcatctactact gctaagatggtttgaaaagtacccagcaggtgagatatgttcgggaggtg gctgtgtggcagcgtgtcccaacacgacacaaagcaccccaccctatct gcaatgctcactgcaaggcagtgccgtaaacagctgcaacaggcatcact tctgcataaatgctgtgactcgttagcatgctgcaactgtgtttaaaacc tatgcactccgttaccaaaataatttaagtcccaaataaatccatgcagc ttgcttcctatgccaacatattttagaaagtattcattcttctttaagaa tatgcacgtggatctacacttcctgggatctgaagcgatttatacctcag ttgcagaagcagtttagtgtcctggatctgggaaggcagcagcaaacgtg cccgttttacatttgaacccatgtgacaacccgccttactgagcatcgct ctaggaaatttaaggctgtatccttacaacacaagaaccaacgacagact gcatataaaattctataaataaaaataggagtgaagtctgtttgacctgt acacacagagcatagagataaaaaaaaaaggaaatcaggaattacgtatt tctataaatgccatatattttactagaaacacagatgacaagtatatac aacatgtaaatccgaagttatcaacatgttaactaggaaaacatttacaa gcatttgggtatgcaactagatcatcaggtaaaaaatcccattagaaaaa tctaagcctcgccagtttcaaaggaaaaaaaccagagaacgctcactact tcaaaggaaaaaaaataaagcatcaagctggcctaaacttaataaggtat ctcatgtaacaacagctatccaagctttcaagccacactataaataaaaa cctcaagttccgatcaacgttttccataatgcaatcagaaccaaaggcat tggcacagaaagcaaaaagggaatgaaagaaaagggctgtacagtttcca aaaggttcttcttttgaagaaatgtttctgacctgtcaaaacatacagtc cagtagaaattttactaagaaaaaagaacaccttacttaaaaaaaaaaaa caacaaaaaaaacaggcaaaaaaacctctcctgtcactgagctgccacca cccaaccaccacctgctgtgggctttgtctcccaagacaaaggacacaca gccttatccaatattcaacattacttataaaaacgctgatcagaagaaat accaagtatttcctcagagactgttatatcctttcatcggcaacaagaga tgaaatacaacagagtgaatatcaaagaaggcggcaggagccaccgtggc accatcaccgggcagtgcagtgcccaactgccgttttctgagcacgcata ggaagccgtcagtcacatgtaataaaccaaaacctggtacagttatatta tggatcc

TABLE 1B

| MAR Element (Accession NO: X52989; SEQ ID NO:2) |
|---|
| gcgctgctga cttctaaac ataaggctgt attgtcttcc |
| tgtaccattg catttcctca ttcccaattt gcacaaggat |
| gtctgggtaa actattcaag aaatggcttt gaaatacagc |
| atgggagctt gtctgagttg gaatgcagag ttgcactgca |
| aaatgtcagg aaatggatgt ctctcagaat gcccaactcc |
| aaaggattta tatgtgtata tagtaagcag tttcctgatt |
| ccagcaggcc aaagagtctg ctgaatgttg cgttgccgga |
| gacctgtatt tctcaacaag gtaagatggt atcctagcaa |
| ctgcggattt taatacattt tcagcagaag tacttagtta |
| atctctacct ttagggatcg tttcatcatt tttagatgtt |
| atacttgaaa tactgcataa cttttagctt tcatggttc |
| ctttttttca gccttaggga gactgttaag caatttgctg |
| tccaacttt gtgttggtct taaactgcaa tagtagttta |
| ccttgtattg aagaaataaa gaccattttt atattaaaaa |
| atacttttgt ctgtcttcat tttgacttgt ctgatatcct |
| tgcagtgctc attatgtcag ttctgtcaga tattcacaca |
| tcaaaactta acgtgagctc |

TABLE 1C

| MAR Element (Accession No: X84223; SEQ ID NO:3) |
|---|
| aagcttcttt ggaaatacac cgacttgatt gaagtctctt |
| gaagatagta aacagtactt acctttgatc ccaatgaaat |
| cgagcatttc agttgtaaaa gaattccgcc tattcatacc |
| atgtaatgta attttacacc cccagtgctg acactttgga |
| atatattcaa gtaatagact ttggcctcac cctcttgtgt |
| actgtatttt gtaatagaaa atatttaaaa ctgtgcatat |
| gattattaca ttatgaaaga gacattctgc tgatcttcaa |
| atgtaagaaa atgaggagtg cgtgtgcttt tataaataca |
| agtgattgca aattagtgca ggtgtcctta aaaaaaaaaa |
| aaagtaatat aaaaaggacc aggtgtttta caagtgaaat |
| acattcctat ttggaaaaca gttacatttt tatgaagatt |
| accagcgct |

TABLE 1D

| MAR Element (Accession No: X98408; SEQ ID NO:4) |
|---|
| ggatccataa tataactgta ccaggttttg gtttattaca |
| tgtgactgac ggcttcctat gcgtgctcag aaaacggcag |
| ttgggcactg cactgcccgg tgatggtgcc acggtggctc |

TABLE 1D-continued

| MAR Element (Accession No: X98408; SEQ ID NO:4) |
|---|
| ctgccgcctt ctttgatatt cactctgttg tatttcatct |
| cttgttgccg atgaaaggat ataacagtct ctgaggaaat |
| acttggtatt tcttctgatc agcgttttta taagtaatgt |
| tgaatattgg ataaggctgt gtgtcctttg tcttgggaga |
| caaagcccac agcaggtggt ggttgggtgg tggcagctca |
| gtgacaggag aggttttttt gcctgttttt tttgttgttt |
| ttttttttta agtaaggtgt tctttttct tagtaaaatt |
| tctactggac tgtatgtttt gacaggtcag aaacatttct |
| tcaaaagaag aaccttttgg aaactgtaca gcccttttct |
| ttcattccct ttttgctttc tgtgccaatg cctttggttc |
| tgattgcatt atggaaaacg ttgatcggaa cttgaggttt |
| ttatttatag tgtggcttga aagcttggat agctgttgtt |
| acatgagata ccttattaag tttaggccag cttgatgctt |
| tatttttttt cctttgaagt agtgagcgtt ctctggtttt |
| tttcctttga aactggcgag gcttagattt ttctaatggg |
| attttttacc tgatgatcta gttgcatacc caaatgcttg |
| taaatgtttt cctagttaac atgttgataa cttcggattt |
| acatgttgta tatacttgtc atctgtgttt ctagtaaaaa |
| tatatggcat ttatagaaat acgtaattcc tgatttcctt |
| ttttttttat ctctatgctc tgtgtgtaca ggtcaaacag |
| acttcactcc tattttatt tatagaattt tatatgcagt |
| ctgtcgttgg ttcttgtgtt gtaaggatac agccttaaat |
| ttcctagagc gatgctcagt aaggcgggtt gtcacatggg |
| ttcaaatgta aaacgggcac gtttgctgct gccttcccag |
| atccaggaca ctaaactgct tctgcaactg aggtataaat |
| cgcttcagat cccaggaagt gtagatccac gtgcatattc |
| ttaaagaaga atgaatactt tctaaaatat gttggcatag |
| gaagcaagct gcatggattt atttgggact taaattattt |
| tggtaacgga gtgcataggt tttaaacaca gttgcagcat |
| gctaacgagt cacagcattt atgcagaagt gatgcctgtt |
| gcagctgttt acggcactgc cttgcagtga gcattgcaga |
| taggggtggg gtgctttgtg tcgtgttggg acacgctgcc |
| acacagccac ctcccgaaca tatctcacct gctgggtact |
| tttcaaacca tcttagcagt agtagatgag ttactatgaa |
| acagagaagt tcctcagttg gatattctca tgggatgtct |
| ttttttccat gttgggcaaa gtatgataaa gcatctctat |
| ttgtaaatta tgcacttgtt agttcctgaa tcctttctat |

TABLE 1D-continued

MAR Element (Accession No: X98408; SEQ ID NO:4)

agcaccactt attgcagcag gtgtaggctc tggtgtggcc tgtgtctgtg cttcaatctt ttaagctt

TABLE 1E

MAR Element (Accession No: AJ277960; SEQ ID NO:5)

aggtcactgt gacctagatc cgcaggtcac tgtgacctac
atctgatatc atcgtcgacg gtatcgataa gcttcgaccg
atccggcccc gcccagcgtc ttgtcattgg cgaattcgaa
cacgcagatg cagtcgggc ggcgcggtcc gaggtccact
tcgcatatta aggtgacgcg tgtggcctcg aacaccgagc
gaccctgcag cgaccgctt aacagcgtca acagcgtgcc
gcagatctcg agagatctcg aggcatgcaa gcttggcatt
ccggtactgt tggtaaaatg gaagacgcca aaaacataaa
gaaaggcccg gcgccattct atcctctaga ggatggaacc
gctggagagc aactgcataa ggctatgaag agatacgccc
tggttcctgg aacaattgct tttacagatg cacatatcga
ggtgaacatc acgtacgcgg aatacttcga aatgtccgtt
cggttggcag aagctatgaa acgatatggg ctgaatacaa
atcacagaat cgtcgtatgc agtgaaaact ctcttcaatt
ctttatgccg gtgttgggcg cgttatttat cggagttgca
gttgcgcccg cgaacgacat ttataatgaa cgtgaattgc
tcaacagtat gaacatttcg cagcctaccg tagtgtttgt
ttccaaaaag gggttgcaaa aattttgaa cgtgcaaaaa
aaattaccaa taatccagaa aattattatc atggattcta
aaacggatta ccagggattt cagtcgatgt acacgttcgt
cacatctcat ctacctcccg gttttaatga atacgatttt
gtaccagagt cctttgatcg tgacaaaaca attgcactga
taatgaattc ctctggatct actgggttac ctaagggtgt
ggcccttccg catagaactg cctgcgtcag attctcgcat
gccagagatc ctatttttgg caatcaaatc attccggata
ctgcgatttt aagtgttgtt ccattccatc acggttttgg
aatgtttact acactcggat atttgatatg tggatttcga
gtcgtcttaa tgtatagatt tgaagaagag ctgtttttac
gatcccttca ggattacaaa attcaaagtc gttgctagt
accaacccta ttttcattct tcgccaaaag cactctgatt
gacaaatacg atttatctaa tttacacgaa attgcttctg
gggcgcacc ctttcgaaa gaagtcgggg aagcggttgc TABLE 1E-continued MAR Element (Accession No: AJ277960; SEQ ID NO:5)

aaaacgcttc catcttccag ggatacgaca aggatatggg
ctcactgaga ctacatcagc tattctgatt acacccgagg
gggatgataa accgggcgcg gtcggtaaag ttgttccatt
ttttgaagcg aaggttgtgg atctggatac cgggaaaacg
ctgggcgtta atcagagagg cgaattatgt gtcagaggac
ctatgattat gtccggttat gtaaacaatc cggaagcgac
caacgccttg attgacaagg atggatggct acattctgga
gacatagctt actgggacga agacgaacac ttcttcatag
ttgaccgctt gaagtcttta attaaataca aaggatatca
ggtggccccc gctgaattgg aatcgatatt gttacaacac
cccaacatct tcgacgcggg cgtggcaggt cttcccgacg
atgacgccgg tgaacttccc gccgccgttg ttgttttgga
gcacggaaag acgatgacgg aaaaagagat cgtggattac
gtggccagtc aagtaacaac cgcgaaaaag ttgcgcggag
gagttgtgtt tgtggacgaa gtaccgaaag gtcttaccgg
aaaactcgac gcaagaaaaa tcagagagat cctcataaag
gccaagaagg gcggaaagtc caaattgtaa aatgtaactg
tattcagcga tgacgaaatt cttagctatt gtaatactgc
gatgagtggc agggcggggc gtaattttt taaggcagtt
attggtgccc ttaaacgcct ggtgctacgc ctgaataagt
gataataagc ggatgaatgg cagaaattcg ccggatcttt
gtgaaggaac cttacttctg tggtgtgaca taattggaca
aactacctac agagatttaa agctctaagg taaatataaa
attttttaagt gtataatgtg ttaaactact gattctaatt
gtttgtgtat tttagattcc aacctatgga actgatgaat
gggagcagtg gtggaatgcc tttaatgagg aaaacctgtt
ttgctcagaa gaaatgccat ctagtgatga tgaggctact
gctgactctc aacattctac tcctccaaaa agaagagaa
aggtagaaga cccaaggac tttccttcag aattgctaag
tttttttgagt catgctgtgt ttagtaatag aactcttgct
tgctttgcta tttacaccac aaaggaaaaa gctgcactgc
tatacaagaa aattatgaa aaatattctg taacctttat
aagtaggcat aacagttata atcataacat actgttttt
cttactccac acaggcatag agtgtctgct attaataact
atgctcaaaa attgtgtacc tttagctttt taatttgtaa
aggggttaat aaggaatatt tgatgtatag tgccttgact
agagatcata atcagccata ccacatttgt agaggtttta
cttgctttaa aaaacctccc acacctcccc ctgaacctga

TABLE 1E-continued

MAR Element (Accession No: AJ277960; SEQ ID NO:5)

```
aacataaaat gaatgcaatt gttgttgtta acttgtttat
tgcagcttat aatggttaca aataaagcaa tagcatcaca
aatttcacaa ataaagcatt tttttcactg cattctagtt
gtggtttgtc caaactcatc aatgtatctt atcatgtctg
gatccgtcga gggggatcca ctagttctag agcggccgcc
accgggatcc ataatataac tgtaccaggt tttggtttat
tacatgtgac tgacggcttc ctatgcgtgc tcagaaaacg
gcagttgggc actgcactgc ccggtgatgg tgccacggtg
gctcctgccg ccttctttga tattcactct gttgtatttc
atctcttgtt gccgatgaaa ggatataaca gtctctgagg
aaatacttgg tatttcttct gatcagcgtt tttataagta
atgttgaata ttggataagg ctgtgtgtcc tttgtcttgg
gagacaaagc ccacagcagg tggtggttgg gtggtggcag
ctcagtgaca ggagaggttt ttttgcctgt ttttttttgtt
gttttttttt tttaagtaag gtgttcttttt ttcttagtaa
aatttctact ggactgtatg ttttgacagg tcagaaacat
ttcttcaaaa gaagaacctt ttggaaactg tacagcccctt
ttctttcatt ccctttttgc tttctgtgcc aatgcctttg
gttctgattg cattatggaa aacgttgatc ggaacttgag
gtttttattt atagtgtggc ttgaaagctt ggatagctgt
tgttacatga gataccttat taagtttagg ccagcttgat
gctttatttt ttttcctttg aagtagtgag cgttctctgg
tttttttcct ttgaaactgg cgaggcttag attttttctaa
tgggatttttt tacctgatga tctagttgca tacccaaatg
cttgtaaatg ttttcctagt taacatgttg ataacttcgg
atttacatgt tgtatatact tgtcatctgt gtttctagta
aaaatatatg gcatttatag aaatacgtaa ttcctgatttt
cctttttttt ttatctctat gctctgtgtg tacaggtcaa
acagacttca ctcctatttt tatttataga attttatatg
cagtctgtcg ttggttcttg tgttgtaagg atacagcctt
aaatttccta gagcgatgct cagtaaggcg ggttgtcaca
tgggttcaaa tgtaaaacgg gcacgtttgc tgctgccttc
ccagatccag gacactaaac tgcttctgca actgaggtat
aaatcgcttc agatcccagg aagtgtagat ccacgtgcat
attcttaaag aagaatgaat actttctaaa atatgttggc
ataggaagca agctgcatgg atttatttgg gacttaaatt
attttggtaa cggagtgcat aggttttaaa cacagttgca
gcatgctaac gagtcacagc atttatgcag aagtgatgcc
tgttgcagct gtttacggca ctgccttgca gtgagcattg
cagataggggg tggggtgctt tgtgtcgtgt tgggacacgc
tgccacacag ccacctcccg aacatatctc acctgctggg
tacttttcaa accatcttag cagtagtaga tgagttacta
tgaaacagag aagttcctca gttggatatt ctcatgggat
gtcttttttc ccatgttggg caaagtatga taaagcatct
ctatttgtaa attatgcact tgttagttcc tgaatccttt
ctatagcacc acttattgca gcaggtgtag gctctggtgt
ggcctgtgtc tgtgcttcaa tcttttaagc tt
```

The invention provides a method of transforming one or more eukaryotic cells by co-transfecting two or more nucleic acid vectors into the cell. These two or more vectors include a first vector containing a gene encoding a desired protein to be expressed by the cell and a promoter controlling the expression of this gene, as well as a second vector containing at least one chromatin element such as a MAR element (e.g., a chicken lysozyme MAR element). The nucleic acid sequences of SEQ ID NOs 1–5 are useful as MAR elements of the present invention. In various embodiments, the first and second vectors are integrated into the host cell's chromosomal DNA. Those skilled in the art will recognize that any means of transfection can be used in accordance with the methods disclosed herein. In some embodiments, the first vector contains a single chromatin element (e.g. a MAR element). In some other embodiments, the invention provides a method of transforming one or more eukaryotic cells by co-transfecting three or more nucleic acid vectors into the cell. Additionally transfected vectors may include, e.g., genes encoding for structural or regulatory proteins, or selection genes.

In some embodiments, enhancer elements are optionally included in one or more of the vectors of the invention.

The ratio of the first and second vectors may be adapted as required for the use of specific cell types, and is routine experimentation to one of ordinary skill in the art. A non-limiting exemplary range of molar ratios of the first vector to second vector is between about 1:2 and about 1:10. However, other ratios are also envisioned by this invention, including 2:1, 1:1, 1:20, 1:50, 1:100 and 1:1000 or more.

The present invention also envisions the use of butyrate to modulate (e.g. increase) transgene expression (see, e.g., Example 6, infra). Butyrate may be added to the cell prior to, concomitant with, or following addition of the nucleic acid vectors. One skilled in the art would easily determine the most advantageous time and concentration of butyrate for the cell line being transfected. For example, butyrate may be added in a concentration of about 0.1 mM to about 1 M. Preferably, in an amount of about 1–500 mM, 1–250 mM, 1–100 mM, 1–75 mM, 1–50 mM, 1–25 mM, 1–20 mM, 1–15 mM, 1–14 mM, 1–13 mM, 1–12 10 mM. Those skilled in the art will recognize that the specific effect(s) of butyrate depend upon the cell type used in the co-transfection, and that the addition of butyrate may or may not affect the proliferation or differentiation of the transfected cells. Butyrate may be added in the form of sodium butyrate or any other compound known to those skilled in the art.

The invention further encompasses the co-transfection of the eukaryotic cell with one or more unlinked nucleic acid vectors in addition to the first vector containing a gene encoding a desired protein to be expressed by the cell, the expression of this gene is controlled by a promoter, and the second vector containing at least one chromatin element (e.g., a chicken lysozyme MAR element). The additional vector or vectors may encode for selection genes or product genes or both. In such embodiments where three unlinked vectors are co-transfected, the ratio of first, second and third vectors may be adapted as required for the use of specific cell types. Determination of the ratio of these vectors is a matter of is routine experimentation to one of ordinary skill in the art. For example, a non-limiting molar ratio range of the first, second and third vectors is between about 1:1.75: 5.5 and about 1:1.75:11. Other ratios including 1:2:20, 1:2:50, 1:2:100 or 1:2:1000 or more, are also envisioned by this invention.

Also provided are methods to select a transfected eukaryotic cell that expresses a desired level of a gene encoding for a desired protein. In certain instances, these cells may produce larger quantities of the desired protein (such as for therapeutic protein production and purification) or smaller quantities of protein (such as for functional analysis). In a preferred embodiment, the expression of a gene in a first cell co-transfected with a first vector containing a gene encoding a desired protein to be expressed by the cell, and a second vector containing at least one chromatin element such as a MAR element, is compared with the expression of the gene in a second cell transfected with only the first vector, and the first cell is selected if the level of expression of the first gene is different between the first and the second cells. This method is useful to select those transfected cells in which the presence of the second vector containing the MAR element is advantageous (e.g., causes an increase of) to the expression of the desired gene.

The present invention also encompasses cell transfection compositions, which can be used to increase the expression of a gene that encodes a desired protein in a cell. In one embodiment, this cell transfection composition includes a vector containing at least one MAR element (e.g., a chicken lysozyme MAR element). In another embodiment, the cell transfection composition may include a first vector containing a gene encoding a desired protein or a portion thereof to be expressed by the cell, and a second vector containing at least one chromatin element such as a MAR element. The cell transfection composition may also additionally contain butyrate, for example in a concentration of about 10 mM, about 100 mM or about 1 M butyrate.

The present invention also encompasses a eukaryotic cell that has been co-transfected, containing a first vector having a first promoter and a first gene encoding a desired gene or a portion thereof, and a second vector comprising a MAR element. As an embodiment of the invention, the first and/or the second vectors are integrated into the chromosomal DNA of the eukaryotic cell. The co-transfected eukaryotic cell may be a butyrate-treated cell. The invention also encompasses a eukaryotic cell that has been co-transfected, containing two or more vectors, a first vector having a first promoter, a first gene encoding a desired gene or a portion thereof and a MAR element, and a second vector comprising at least one MAR element. The invention further encompasses a eukaryotic cell that has been co-transfected, containing three or more vectors, a first vector having a first promoter and a first gene encoding a desired gene or a portion thereof, a second vector comprising at least one MAR element, and a third vector comprising a second promoter and a second gene encoding a desired gene or a portion thereof. In some embodiments of the invention, the second gene encodes for a selection gene or a gene encoding a detectable gene product (e.g., a fluorescent protein such as green fluorescent protein, or a luminescent protein such as luciferase).

The present invention provides kits for transfecting eukaryotic cells. For example, the kit can have in one or more containers, two or more nucleic acid vectors, the first vector having a promoter and a heterologous gene coding for a desired protein, and the second vector having at least one MAR element, and directions for use thereof. In an embodiment, the invention provides kits, containing in one or more containers, one or more eukaryotic cells containing two or more nucleic acid vectors, the first vector having a promoter, a heterologous gene coding for a desired protein and a MAR element, and the second vector having one or more MAR elements. In an embodiment, the kit additionally comprises butyrate. The vectors of the kits are provided in ratios that one skilled in the art would be able to use on a cell line under study with minimal experimentation.

EXAMPLES

The invention will be further described in the following examples, which do not limit the scope of the invention described in the claims.

Example 1

General Materials and Methods

Plasmid construction. The luciferase expression vectors used to test the chromatin elements are all based on pGL3-Control (Promega). This plasmid contains an SV40 promoter in front of a modified firefly luciferase cDNA, followed by the SV40 late poly(A) signal and the SV40 enhancer. The *Drosophila melanogaster* elements come from the p7, p83 and p 1314 plasmids (Poljak et al., 1994). The 1.8 kb SalI scs (special chromatin structure) BE fragment comes from p83, as well as the 960 bp BamHI-XhoI heat shock 87A locus SAR (hsp SAR). The 500 bp BamHI scs' BE fragment is derived from p7, whereas the 657 bp EcoRI-HinfI histone SAR (his SAR) comes from p1314.

Combinations of these elements were first cloned into the BamHI SalI sites of pGL3-Control. The scs' BE and hsp SAR were cloned as BamHI-EcoRI and EcoRI-SalI fragments respectively, giving pMZ61. Similarly, the BamHI-EcoRI scs' BE fragment and EcoRI-SalI his SAR fragment were inserted to give pMZ62, and the BamHI-EcoRI his SAR and EcoRI-SalI scs' BE were introduced to yield pMZ63. Chromatin elements were then cloned in sites upstream of the luciferase expression cassette. Construct pMZ67-1 was obtained by cloning the KpnI-BamHI hsp SAR and BamHI scs BE fragments into the KpnI BglII sites of pMZ61, whereas pMZ70-1 resulted from cloning the same fragments into pMZ62. Vector pMZ71 was constructed by introducing the KpnI-EcoRI his SAR and EcoRI-BamHI scs' BE fragments in the KpnI BglII sites of pMZ61, whereas pMZ68 resulted from cloning the same fragments in pMZ62. Lastly, pMZ69 was obtained by cloning the XbaI-EcoRI scs' BE and EcoRI-BamHI his SAR fragments in the NheI BglII sites of pMZ63. The 2.95 kb BamHI-XbaI chicken lysozyme MAR (lys MAR) fragment (Phi-Van and Strätling, 1988) is from pUC-B-1-X1 (Wolf Strätling). It was first cloned into the BamHI SalI sites of pGL3-Control, giving pMZ50. Construct pMZ52 was obtained by inserting a second MAR as a KpnI-XbaI fragment into the KpnI NheI-sites of pMZ50. The mouse T-cell receptor α LCR 6 kb subregion (Ortiz et al., 1997) originated from p3'LCR-72 (Astar Winoto). It was cloned into the SalI and filled-in BamHI sites of pGL3-Control as a SalI and filled-in EcoRI fragment, giving pMZ74. The 2 kb NheI fragment from S1 LIP (Ueli Schibler) presumably encompasses the rat LAP LCR (Talbot et al., 1994). It was cloned in both orientations as a KpnI-filled in NotI fragment into the KpnI SmaI sites of pGL3-Control to give pMZ44 and pMZ45.

The immunoglobulin expression vectors, pMZ57 and pMZ36, are identical to those described elsewhere (Miescher et al.), except that the human cytomegalovirus MIE promoter/enhancer drives light and heavy chain expression. The plasmids for the regulated expression system, pEF1-TetRNLS-TR450W, pPGK-TetRNLS-TR450W, pSV-TetRNLS-KoxW, pVG-GTTI-Luc+, p5xGTTI-GVP and p5xGTTI-mEpoiresβGeo have previously been described (Imhof et al., 2000) All plasmids were constructed using standard techniques.

CHO cell culture and transfection. The CHO DG44 cell line (Urlaub et al., 1983) was cultivated in DMEM:F12 (Gibco-BRL) supplemented with HT (Gibco-BRL) and either 2 or 10% FBS (Gibco-BRL). Pools of stable CHO cells expressing luciferase were obtained by transfection with polyethyleneimine (PEI) (Boussif et al., 1995). Cells were seeded in 6-well plates at 500–750 000 cells/well and allowed to attach overnight. Equimolar amounts of PvuI-linearized test constructs, corresponding to 2–3 µg pGL3-Control, were co-transfected with pSV2neo (CLONTECH Laboratories, Inc.) in a 10:1 molar ratio, with transfection mixes brought to a total of 10 µg with either pUC19 or pBluescript. Plasmid DNA was diluted in 150 mM NaCl, and an equal volume of 150 mM NaCl solution containing 35 µl 10 mM PE125 (Fluka) was added. Following a 15 min. incubation at room temperature, the transfection mix was added to the cells. The medium was either replaced or supplemented with fresh medium after 4 hours. After 48 hours, cells were washed with PBS, trypsinized and replated in medium supplemented with 700 µg/ml geneticin (G-418 sulphate, Gibco-BRL). Subsequent medium changes were carried out with medium supplemented with 500 µg/ml geneticin, with pools of clones assayed after 13 and 15 days of selection. Individual clones expressing luciferase were picked after 12–14 days of selection, and maintained in selective medium prior to analysis.

Stable CHO clones expressing human anti-Rhesus D IgG1 antibody were obtained by co-transfecting the light chain vector pMZ57, the heavy chain vector pMZ36 and either the MAR-bearing plasmid pUC-B-1-X1, or pUC18 as a control. A total of 2.5 µg of DNA per well, with either a 1:1.75:5.5 or 1:1.75:11 molar ratio of pMZ57:pMZ36:pUC-B-1-X1 was used, corresponding to a 2:1 and 4:1 molar ratio of MAR: antibody plasmids respectively. Cells were seeded in a 12-well plate at 140 000 cells/well, 18 h prior to transfection using an optimized calcium-phosphate precipitation method (Jordan et al., 1996). A glycerol shock (10% glycerol in PBS 1X) was applied 3 hours after transfection, and cells were maintained for 2 days under non selective conditions in medium supplemented with 8% FCS. Selection in MEM (GHT-) medium (Sigma), supplemented with 100 µM L-Proline, 5% dialyzed fetal bovine serum (Gibco-BRL) and buffered with 10 mM HEPES, was carried out upon replating the cells in 10 cm dishes. Colonies arose after 10–14 days, and stable clones were transferred to 24-well plates. After 8 days, culture supernatants were diluted two- and ten-fold, and antibody concentration determined by ELISA.

C2C12 cell culture and transfection. The C2C12 cell line was cultured in DMEM (Gibco-BRL) supplemented with 10% FCS. Stable C2C12 clones expressing the repressor were obtained by co-transfection using Lipofectin™ (Gibco-BRL) of TK-Hyg, one of the repressor expression plasmids, pEF1-TetRNLS-TR450W, pPGK-TetRNLS-TR450W, pSV-TetRNLS-KoxW, and the MAR plasmid pUC-B-1-X1, in a 1:4 molar ratio. Clones were picked after selection for 9 days with 200 µg/ml hygromycin B (Gibco-BRL). Transient transfection with pVG-GTTI-Luc+, and pCMVβgal (MacGregor and Caskey, 1989) as an internal standard for transfection efficiency, was performed in triplicate essentially as described previously (Imhof et al., 2000). The medium, with or without 100 ng/ml doxycycline hydrochloride (Sigma), was changed every 24 hours, and cells were harvested 48 hours post-transfection. The pool of clones with the pEF1-TetRNLS-TR450W repressor was co-transfected with the activator expression plasmid p5xGTTI-GVP, the reporter plasmid p5xGTTI-mEpoiresβGeo and the MAR plasmid pUC-B1-X-1. After selection with 500 µg/ml geneticin, flow cytometric analysis of the pool of clones using fluorescein di-β-D galactopyranoside (Molecular Probes) was performed according to the manufacturer. Cells with an intermediate expression of β-galactosidase were sorted, and these clones were expanded in medium without doxycycline. These clones were screened for induction in the presence of 100 ng/ml doxycycline hydrochloride, and those expressing β-galactosidase were selected. Following culture in medium without doxycycline hydrochloride, the clones were assayed in the presence and absence of doxycycline.

Cell lysates and reporter assays. Cell extracts were prepared as follows for luciferase and protein measurements. Cells were washed with PBS and incubated with 100 µl lysis buffer (25 mM Tris-phosphate, pH 7.8, 2 mM DTT, 2 mM CDTA, 10% glycerol, 0.5% Triton X-100) for 20 min at room temperature. Luciferase measurements were carried out with 20 µl of extract in white 96 well plates. The constant glow type assay was performed in an EG&G Berthold Microplate 96V luminometer, using the reagents described in the Luciferase Assay Reagent protocol (Promega). For each well, 100 µl substrate solution was added by injection. After a delay of 2 sec light emission was measured for 2 seconds. Colorimetric determination of β-galactosidase activity was performed as previously described (Imhof et al., 2000). Colorimetric determination of protein content was performed by adding a mix of 155 µl water and 40 µl protein assay dye reagent concentrate (BioRad) to 5 µl cell extract in 96 well plates and measuring the absorbance at 595 nm (Spectramax 340, Molecular Devices). All absorbance values were within the linear range of a standard curve established with BSA. Luciferase values were normalized with respect to protein content for CHO clones. For the C2C12 clones, the luciferase values were normalized with respect to β-galactosidase activity, and the β-galactosidase values with the protein content. Human immunoglobulin secreted into the medium was measured by a sandwich ELISA, with unconjugated goat anti-human kappa light chain antibody and alkaline phosphatase-conjugated goat anti-human IgGγ as capture and detection antibodies respectively (BioSource).

Southern and plasmid rescue analyses. Genomic DNA for Southern analysis was isolated with Nucleospin C+T (Macherey & Nagel, Germany) according to the manufacturer's instructions. Aliquots (4 μg) were digested to completion with EcoRI, separated by agarose gel electrophoresis, and blotted onto Hybond N+ membranes (Amersham, England). The full-length MAR probe was isolated from pUC-B-1-X1 as a BamHI-XbaI fragment. Radiolabeling was performed with HighPrime (Roche, Switzerland).

For the plasmid rescue experiments, episomal DNA was isolated from stable cell lines generated by the transfection of the IgG1 and MAR vectors, from untransfected CHO DG44 cells, and from cells transiently transfected with pUC-B-1-X1 one week before DNA isolation. Cells were counted, lysed in alkaline conditions and plasmids purified with the Nucleospin kit (Macherey & Nagel, Germany). Competent *E. coli* cells (Electro ax DH10B, Gibco) were electroporated with the plasmid-extract from approximately $10^5$ cells with a BioRad Gene Pulser unit according to the cell supplier's instructions. Transformants were selected on LB plates containing 100 μg/ml ampicillin.

Construction of cis MAR expression vectors. The cis MAR SV40 IgG-kappa and gamma vectors were created by cloning the BamHI-XbaI MAR fragment from pUC-B1-X1 in plasmids pMZ59 and pMZ37, respectively, linearized with EcoRI and BamHI. The XbaI site of the MAR fragment and EcoRI site of pMZ59 and pMZ37 were first blunted with Pfu. To synthesize the cis MAR CMV IgG kappa and gamma vectors, pMZ57 and pMZ36 were first digested with AvaI and KpnI, respectively, blunted with T4DNA polymerase and then cut with BamHI. The XbaI filled BamHI MAR fragment described above was cloned in the latter vectors.

Example 2

Chromatin Elements and Stable Transgene Expression in CHO Cells

The use of structural chromatin components to overcome silencing of stably integrated genes by the surrounding chromosomal environment will prove particularly useful in biotechnology. Unfortunately, fully characterized chromatin elements in higher eukaryotes are rare. Moreover, most of these have not been tested with a heterologous promoter in heterologous cells. Elements which counteract the effect of neighboring chromatin structure on stable transgene expression are expected to raise the average transgene expression in pools of stable clones, where the effects of different integration sites and the number of active copies become averaged.

Single chromatin elements or combinations of chromatin elements were cloned on either, or both sides, of the luciferase expression unit of pGL3-Control as depicted in FIG. 1. Various combinations of *Drosophila melanogaster* SAR and BE elements were tested flanking the reporter expression cassette. These elements had previously been shown to stimulate stable reporter gene expression in HeLa and L cells (Poljak et al., 1994). The chicken lysozyme 5' MAR element (lys MAR), or 'A-element' was cloned flanking the luciferase expression cassette, in a configuration previously shown to confer elevated expression in chicken promacrophage and rat fibroblast cells (Phi-Van et al., 1990; Stief et al., 1989). The mouse T-cell receptor α LCR (TCRα LCR) and the rat liver activated protein LCR (LAP LCR) have both been shown to direct high-level expression in multiple tissues in transgenic mice (Ortiz et al., 1997; Talbot et al., 1994). The position and orientation of the two LCRs with respect to the transgene promoter was as in their original locus.

The chromatin elements had little or no effect on transient expression levels where chromatin structure does not come into play. Pools of stably transfected CHO cells were analyzed for transgene expression (FIG. 1). A modest 2- to 4-fold increase in expression levels was seen for all combinations tested of the Drosophila SAR and BE elements, as well as for the two LCRs tested. The only element tested showing an important increase in stable reporter expression was the chicken lysozyme 5' MAR, which gave a 20-fold increase in luciferase expression as compared to the pGL3-Control construct. In accordance with previous results in chicken cells (Stief et al., 1989), the orientation of the two MAR elements flanking the reporter expression cassette had no effect on transgene expression. Following this initial screening of the chromatin elements in CHO cells, attention was focused on the use of the chicken lysozyme MAR for its usefulness in stable cell line development.

Example 3

Co-transfection of the MAR Improves Stable Transgene Expression

An alternative strategy to cloning the MAR element into the reporter expression vector is that of co-transfecting a MAR element-containing plasmid with the transgene expression vector. The observation that transfection with multiple plasmids appears to result in co-integration of multiple plasmid copies at the same chromosomal site (Wurm et al., 1992) suggests that the MAR element does not need to be physically linked with the transgene expression cassette at the time of transfection. However, the organization of the various integrated plasmids, and how these may recombine to generate the integrated DNA, is not known. A significant increase in stable transgene expression level is observed when MAR elements flank both sides of the reporter gene expression cassette, suggesting that a precise order of the genetic elements is required. While MAR orientation does not affect stable expression, a particular arrangement with defined spacing may be required. Nevertheless, whether co-transfection of the MAR and the plasmid bearing the reporter expression cassette may also result in enhanced stable transgene expression was determined.

Figure 2:
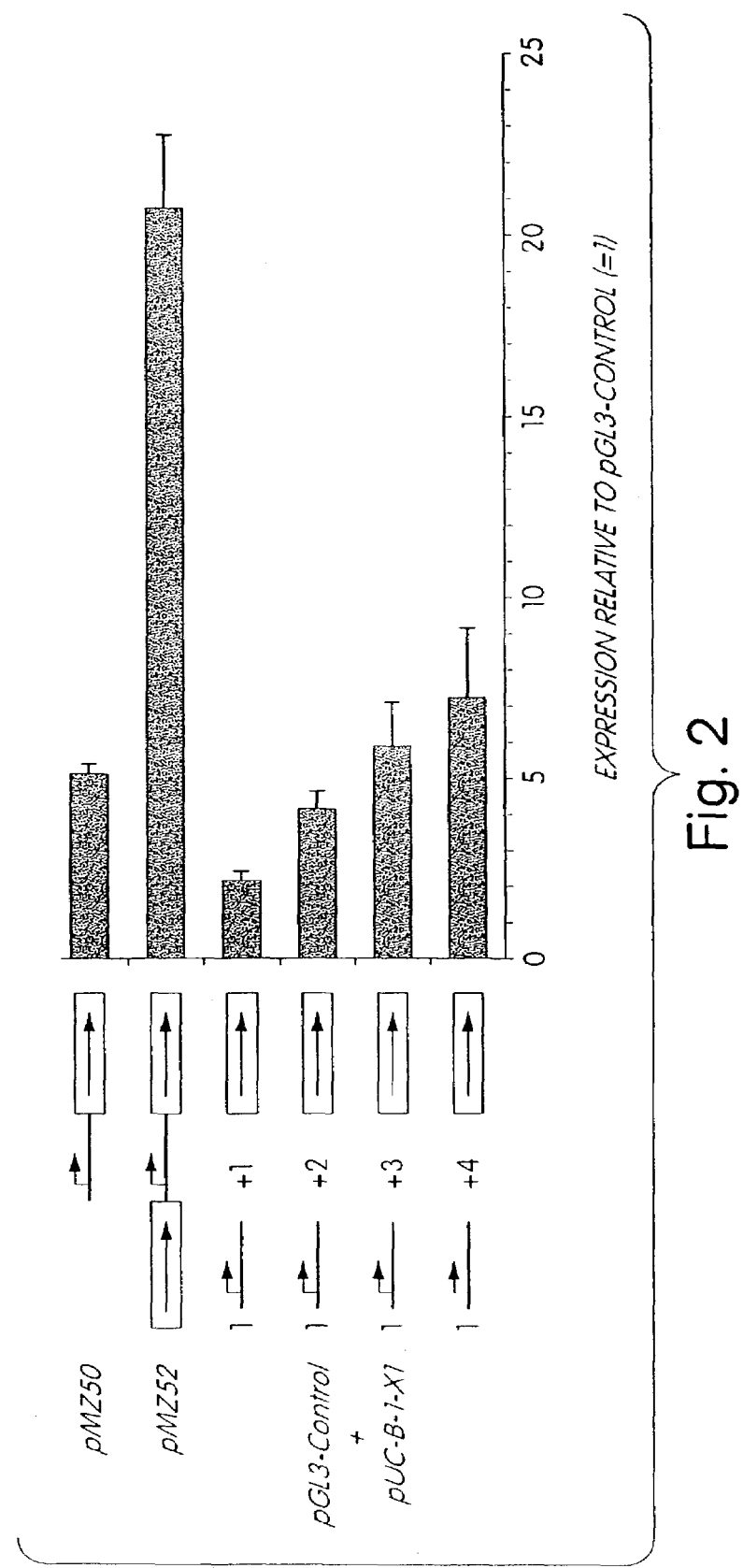
FIG. 2 is a diagram that indicates stable reporter expression using the chicken lysozyme MAR. Constructs with one or two MARs cloned in pGL3-Control (pMZ50 and pMZ52 respectively), as well as the pGL3-Control and pUC-B-1-X1 plasmids in the indicated molar ratios were co-transfected with pSV2neo in CHO cells. The figure shows the luciferase activity of pools of clones, normalized with respect to protein content, and expressed relative to pGL3-Control. Error bars correspond to the standard error, based on at least three independent transfections.

The pGL3-Control reporter was co-transfected with increasing amounts of plasmid pUC-B-1-X1 bearing the chicken lysozyme MAR. FIG. 2 shows the luciferase activity in pools of CHO clones, including results for constructs pMZ50 and pMZ52 with one and two MARs adjacent to the luciferase transcription unit respectively. Comparison of stable expression with pMZ50 and pMZ52 shows that two flanking MARs have a greater effect than a single MAR, when present on the expression plasmid itself. On the other hand, increasing the ratio of MAR plasmid to reporter construct from a molar ratio of 1:1 to 4:1 also results in increased stable expression. Co-transfection of the reporter construct with two MARs yields the same stable expression as the pMZ50 construct with one MAR. Although co-transfection with MARs does not result in stable luciferase expression levels comparable to those obtained with the pMZ52 construct with two flanking MARs, it may also provide an alternative means to enhance stable transgene expression.

Example 4

The MAR Increases the Prevalence of Top Producing Clones

While increased expression in pools of stable clones is indicative of an overall positive effect of the chicken lysozyme MAR on transgene expression, it does not provide information as to the probability of isolating a high producer clone. To address this issue, individual colonies were isolated and the level of expression of the transgene was measured.

Figure 3A:
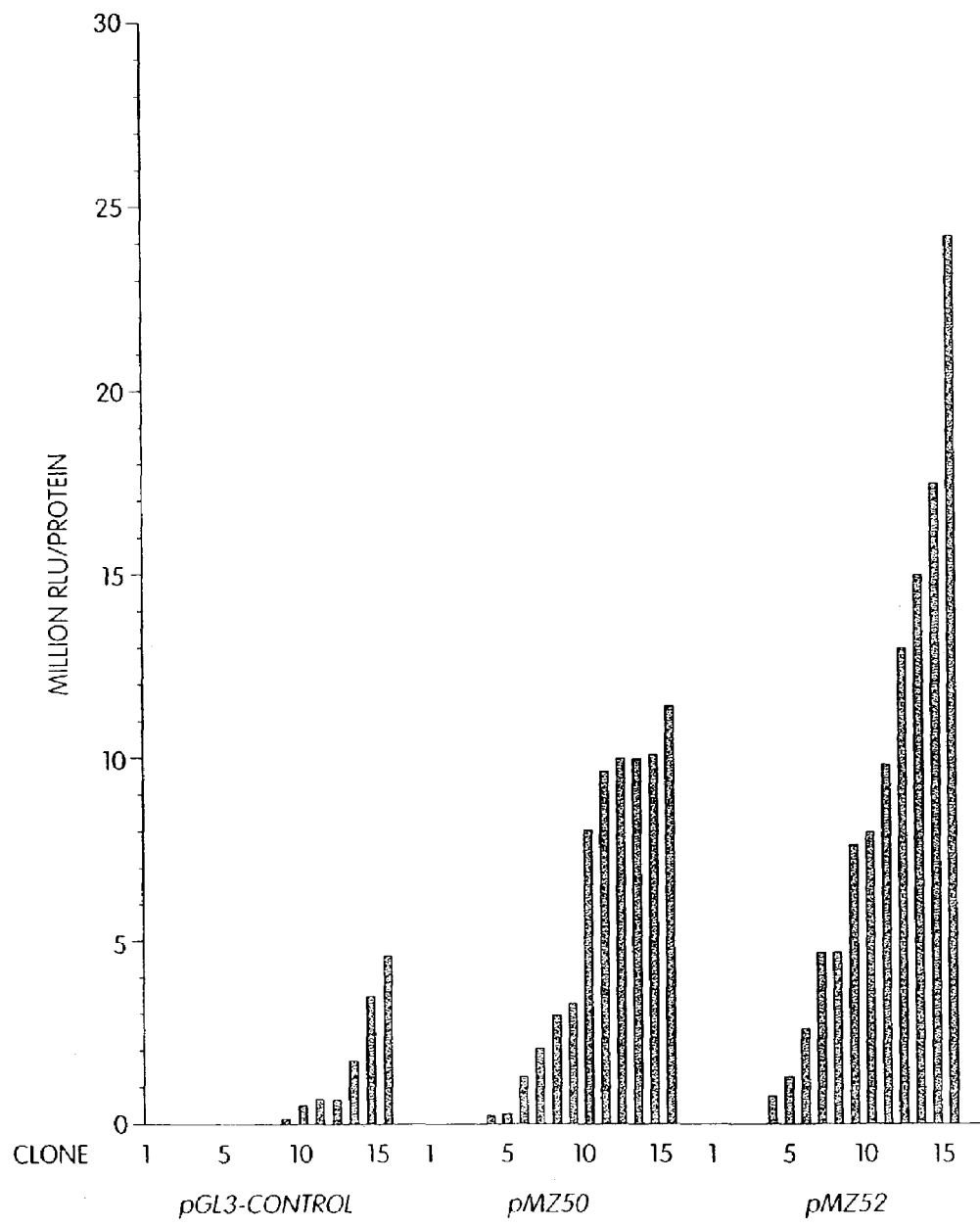
FIG. 3A shows luciferase expression for clones obtained with either pGL3-Control, pMZ50, or pMZ52, corresponding to plasmids bearing no, one, or two chicken lysozyme MARs. Luciferase activity, normalized with respect to protein content, is shown for 15 clones for each construct, ranked from lowest to highest expression level.

CHO cells were transfected with luciferase expression vectors containing none, one, or two MARs, and fifteen individual colonies were randomly isolated and analyzed for each construct. The level of stable luciferase expression of individual colonies, ranked from lowest to highest, is shown in FIG. 3A. Consistent with the results obtained with pools of stable clones, the average expression level of the clones analyzed increases with the number of MARs present on the construct. More importantly, having MARs on the expression construct clearly increases the prevalence of top producing clones. Furthermore, the expression level of the most productive clones is higher for constructs bearing MARs. Thus fewer clones need to be picked and analyzed to identify a high-level production clone when MARs are present on the expression plasmid.

Figure 3B:
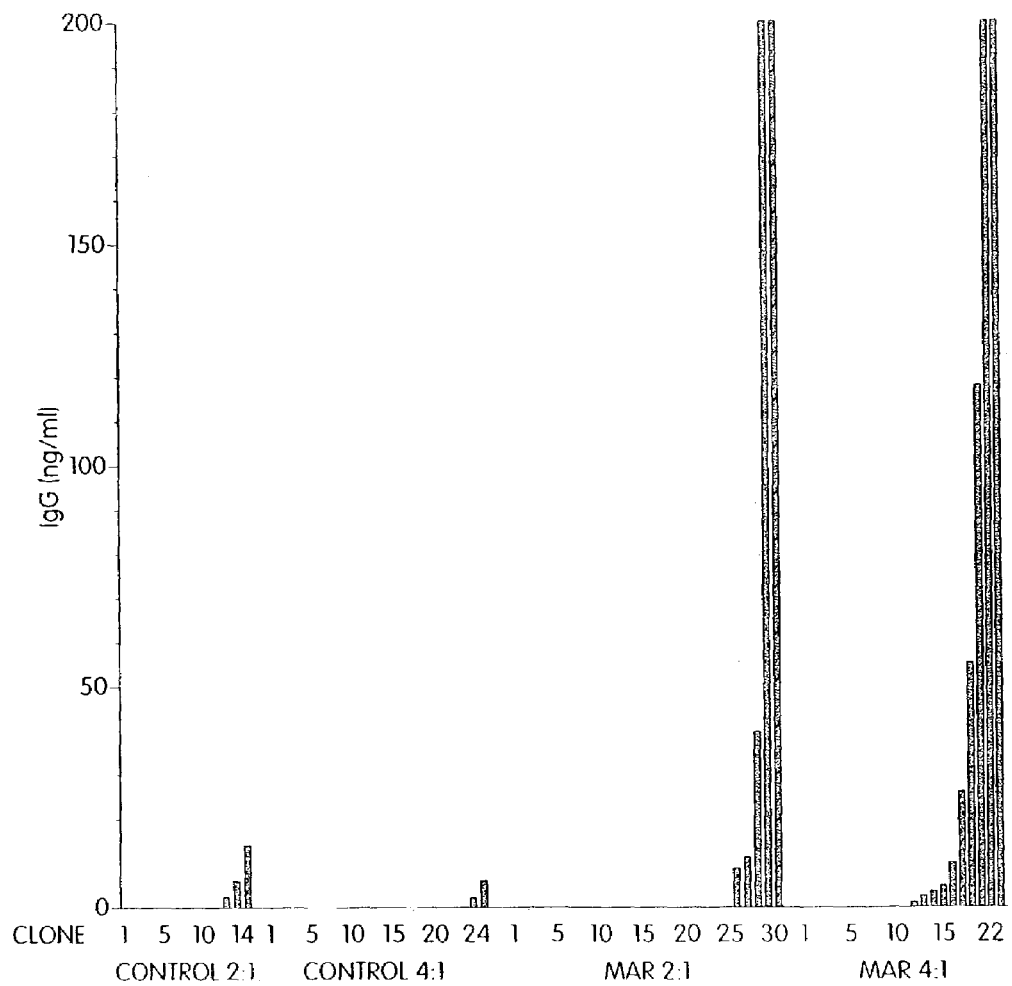
FIG. 3B shows anti-Rhesus D IgG1 antibody expression for clones obtained by co-transfecting the light and heavy chain expression vectors, pMZ57 and pMZ36 respectively, with the indicated molar ratios of either control pUC18 or MAR-bearing pUC-B-1-X1 plasmid. Supernatant antibody concentration is shown for clones ranked from lowest to highest expression level.

A more complex situation occurs with the stable production of a protein composed of multiple subunits expressed from separate plasmids. Instead of cloning the MAR element into each separate vector, whether a simple co-transfection of MARs can also result in improved stable expression levels was examined. To do so, expression vectors for the light and heavy chain of the medically relevant human anti-Rhesus D antibody (Miescher et al., in press) were used. Light and heavy chain expression vectors containing introns, were transfected along with either the pUC-B-1-X1 MAR-bearing plasmid or its pUC backbone as a control. Individual stable CHO colonies were picked and analyzed for antibody expression (FIG. 3B). While few colonies express antibody in the control with pUC18, the proportion of colonies expressing detectable amounts of anti-Rhesus D antibody increases with increasing amounts of MAR.

As seen with the MAR-bearing luciferase constructs, the level of antibody expression of the most productive clones is markedly higher for the MAR colonies than for the controls. Thus the chicken lysozyme MAR increases both the proportion of top producing clones and their expression levels. This is true when the MAR is present on the expression construct, as well as when the MAR is co-transfected with one or more expression constructs. Practically, this means that complex cloning strategies can be bypassed by co-transfection with the MAR element, resulting in the same advantages for stable cell line development. Most importantly, these advantages are also seen upon co-transfection of a MAR element-bearing plasmid with several expression vectors.

Figure 3C:
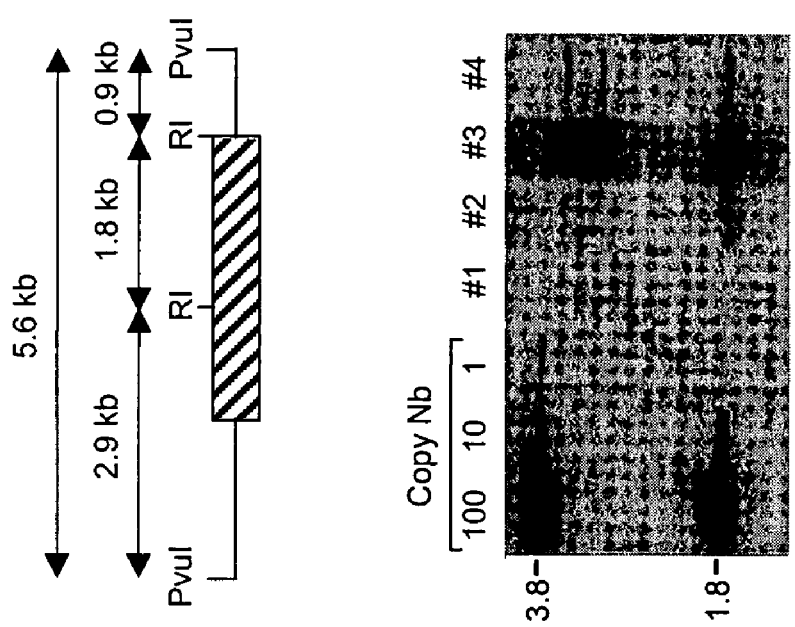
FIG. 3C demonstrates the molecular analysis of anti-Rhesus D antibody-expressing clones. The top panel shows a schematic diagram of the pUC-B-1-X1 vector, with the hatched box corresponding to the MAR sequence. Fragment sizes obtained upon digestion are indicated above the map. The bottom panel shows the results of a Southern blot analysis of four stable cell clones with the MAR from panel B (labeled #1–#4). Genomic DNA was digested with EcoRI and probed with the entire MAR sequence. The molecular mass of fragments is given in kilobase pairs on the left.

In order to confirm that the MAR element has been integrated into the host cell genome, four randomly chosen antibody-expressing clones were analysed by Southern blotting (FIG. 3C). Two fragments, a 1.8 kb MAR fragment and a fragment of variable size corresponding to the remainder of the MAR, are present in all clones and absent in the parent CHO DG44 cell line. Both the light and heavy chain vectors also integrated. A MAR element has recently been shown to enable episomal replication of SV40 ori-containing transfected vectors in CHO cells (Piechaczek et al., 1999). No 3.8 kb band corresponding to pUC-B-1-X1 replicating episomally in CHO cells is detected in the Southern blots. Plasmid rescue experiments were carried out to determine whether the plasmid is present episomally at low copy numbers. Control CHO transient transfections with one copy of the MAR-bearing plasmid pUC-B-1-X1 per cell yielded over 200 colonies. In contrast, the four clones and DG44 yielded a background of up to 4 colonies containing DNA unrelated to the transfected plasmids. Together, these experiments provide evidence that the transfected MAR is not replicating episomally but is integrated into the chromosome of the stable clones.

Example 5

Co-transfection of the MAR to Establish a Stable Regulated Expression System Most currently used regulated gene-expression systems are based on multiple components. In such systems, the stable expression of individual regulatory elements is critical to the control of the expression of the transgene. To date, chromatin elements have rarely been employed in such systems and their use has essentially been restricted to inserting such elements so as to flank the transgene construct (Wang et al., 1997; Wells et al., 1999). It was examined whether a stable regulated expression system can be obtained by co-transfection of the MAR with the components of a regulated expression system (Imhof et al., 2000). This tetracycline-based switch system involves chimeric repressor and activator proteins acting to control transgene transcription.

Figure 4A:
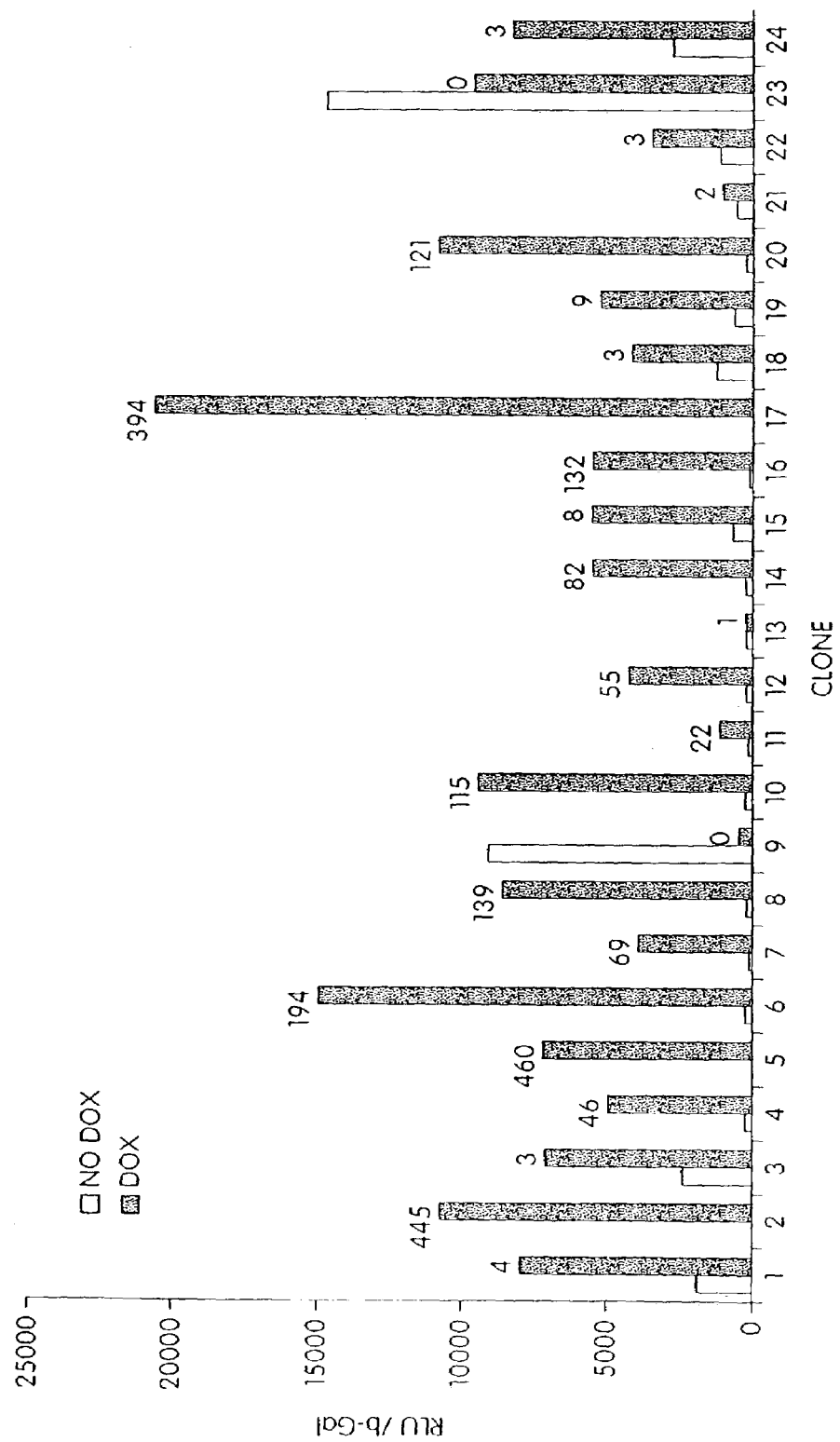
FIG. 4A depicts the screening of randomly picked stable C2C12 clones with the repressor construct. The luciferase activity, normalized with respect to β-galactosidase activity, is shown for 24 clones. White columns correspond to expression in the absence of doxycycline (no dox); black columns correspond to expression induced by the addition of doxycycline (dox), with the fold induction indicated above the black column.
Figure 5A:
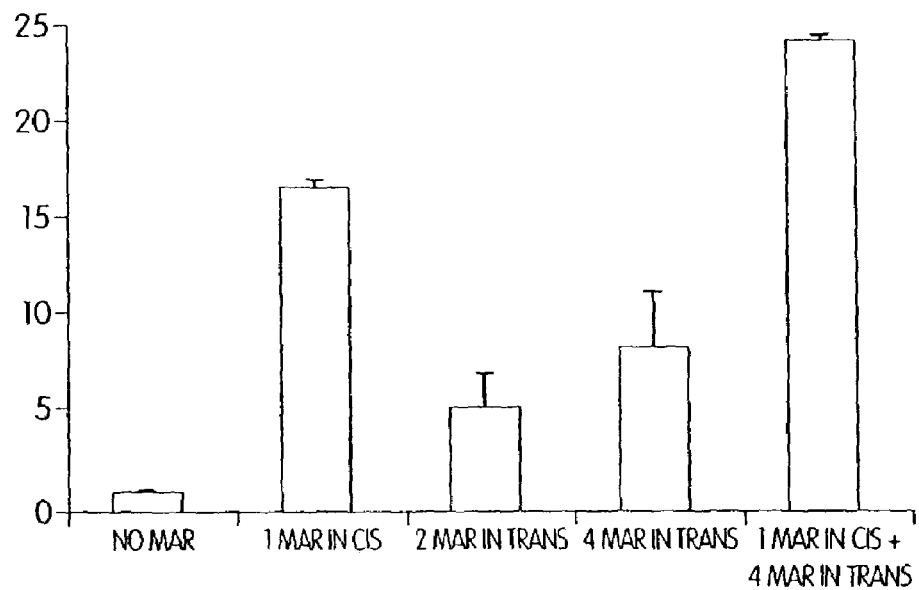
FIG. 5 demonstrates the effect of MARs on IgG productivity in CHO cells. Fold induction of SV40-promoter panel A) and CMV-promoter (panel B) driven expression of recombinant IgG with different combinations of MARs. Results are expressed as means of specific productivity of pools of stably transfected cells from two experiments done in triplicates. Specific productivity of single cell clones with 1 MARs in cis+4 MAR in trans ranged up to 38 pg/cell/day and 40 pg/cell/day with the SV40 and CMV promoter, respectively. Transfections are as generally described in the art, (See e.g., Zahn-Zabal et al., 2001 J. Biotechnol. 87:29, and infra) using plasmids pMZ36, pMZ37, pMZ57 and pMZ59. Plasmid used for the expression of IgG containing one MAR element in cis (1 MAR in cis) were constructed as described in Example 1.
Figure 5B:
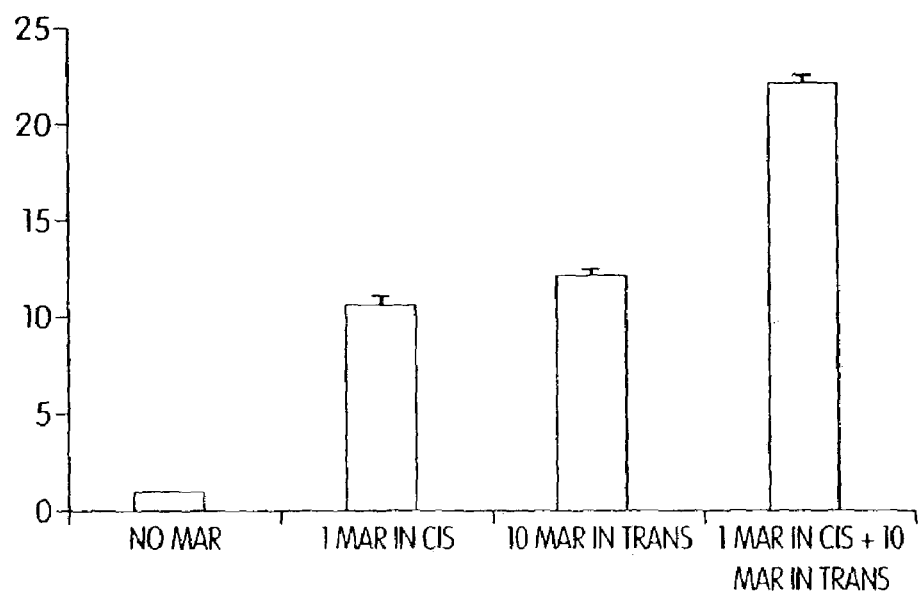
Figure 6:
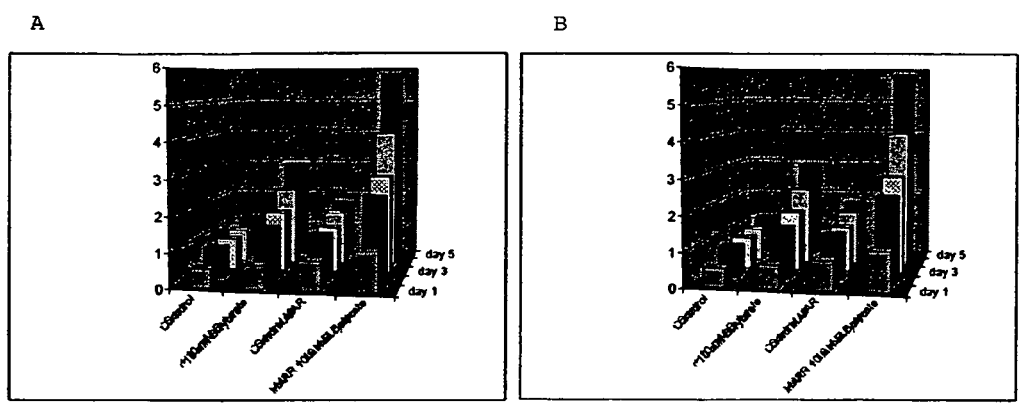
FIG. 6 demonstrates the effect of MAR elements and sodium butyrate on IgG secretion in transiently transfected CHO cells by indicating the time-course accumulation of IgG (μg) per 1.3 ml of culture medium supernatant in a single well of a 24-well plate (the average of triplicate wells is shown).

In a first step, the repressor protein expression vector is stably transfected. Initially, transfection of the vector alone yielded clones in which transgene expression could not be regulated. These clones exhibited unstable repressor protein expression, especially after removal of selective pressure. The three repressor protein expression vectors with the chicken lysozyme 5' MAR plasmid were then separately transfected. The results of a screen of 24 clones, obtained by lipofection, for their ability to induce luciferase expression upon addition of doxycycline is shown in FIG. 4A. A majority of the clones (21 out of 24) show regulated transgene expression, with several exhibiting over 400-fold induction of reporter expression in the presence of doxycycline. Furthermore, regulated gene expression was obtained irrespective of the method of transfection and of the promoter driving repressor protein expression.

In a second step, the activator and reporter constructs are stably transfected into clones expressing the repressor. A pool of clones stably expressing the repressor protein, and from which clones 1 through 8 in FIG. 4A were isolated, was used to this end. The activator and reporter constructs were stably co-transfected with the chicken lysozyme 5' MAR plasmid, and individual cell clones expressing an intermediate level of β-galactosidase were isolated by FACS sorting. These were screened for induction in the presence of doxycycline, and the resulting ten clones tested for the regulation of β-galactosidase expression in the absence and presence of doxycycline after 3 days (FIG. 4B). Five of these clones show regulated expression of β-galactosidase, with an induction ranging from 17- to 45-fold in the presence of doxycycline. Regulated expression of the second transgene, mouse erythropoietin, is also observed (Imhof et al., 2000). Hence cell lines showing regulated expression were obtained by co-transfection of the chicken lysozyme MAR with the elements of the expression system.

Example 6

MAR- and Butyrate-mediated Increased Level of Protein Production in Transiently Transfected CHO Cells A dramatic increase in transgene expression occurs when the chicken 5'-lysozyme MAR is combined with the addition of sodium butyrate to the cell culture medium. Without wishing to be bound by theory, this effect may result from an increased efficiency of DNA transfection, alterations in cell proliferation and/or differentiation, and/or other cellular mechanisms. Butyrate has been used in transient or stable transfections (Gorman et al., 1983 Nucl. Acids Res. 11:7631; Reeves et al., 1985, Nuci. Acids Res. 13:3599).

Vectors: Plasmids encoding anti-RhesusD IgG kappa and gamma chains, pMZ59 and pMZ37, are as previously described for pMZ58 and pMZ36, respectively, except that they contain the SV40 early promoter instead of the CMV promoter (see Example 1). pMZ126 and pMZ127 derive from pMZ59 and pMZ37, but contain in addition one MAR element in cis upstream from the SV40 promoter. pMZ126 and pMZ127 were constructed as follows: pUCB1X1 was digested with XbaI, blunt-ended with Pfu DNA polymerase, digested with BamHI and subcloned directionally in pMZ59 and pMZ37, respectively, that had been first cleaved with EcoRI, blunt-ended with Pfu DNA polymerase, and then digested with BamHI.

Cell culture and transfection: CHO cells were grown as described in Example 1. For transfection, cells were treated as described previously with the following modification: 24 h. after addition of 1 ml of DMEM supplemented with 10% FBS (Gibco, Life Technologies) to each well, 26 µl of 500 mM NaButyrate pH 6,9 in PBS was added to half of the wells where indicated in the figure legend. Aliquots of 2 µl were taken at 24 h. intervals and transfered in 248 µl of blocking solution in a 96-wells plate. IgG titer was determined as described previously by double sandwich ELISA.

Example 7

MAR Element Multimerization

Figure 7A:
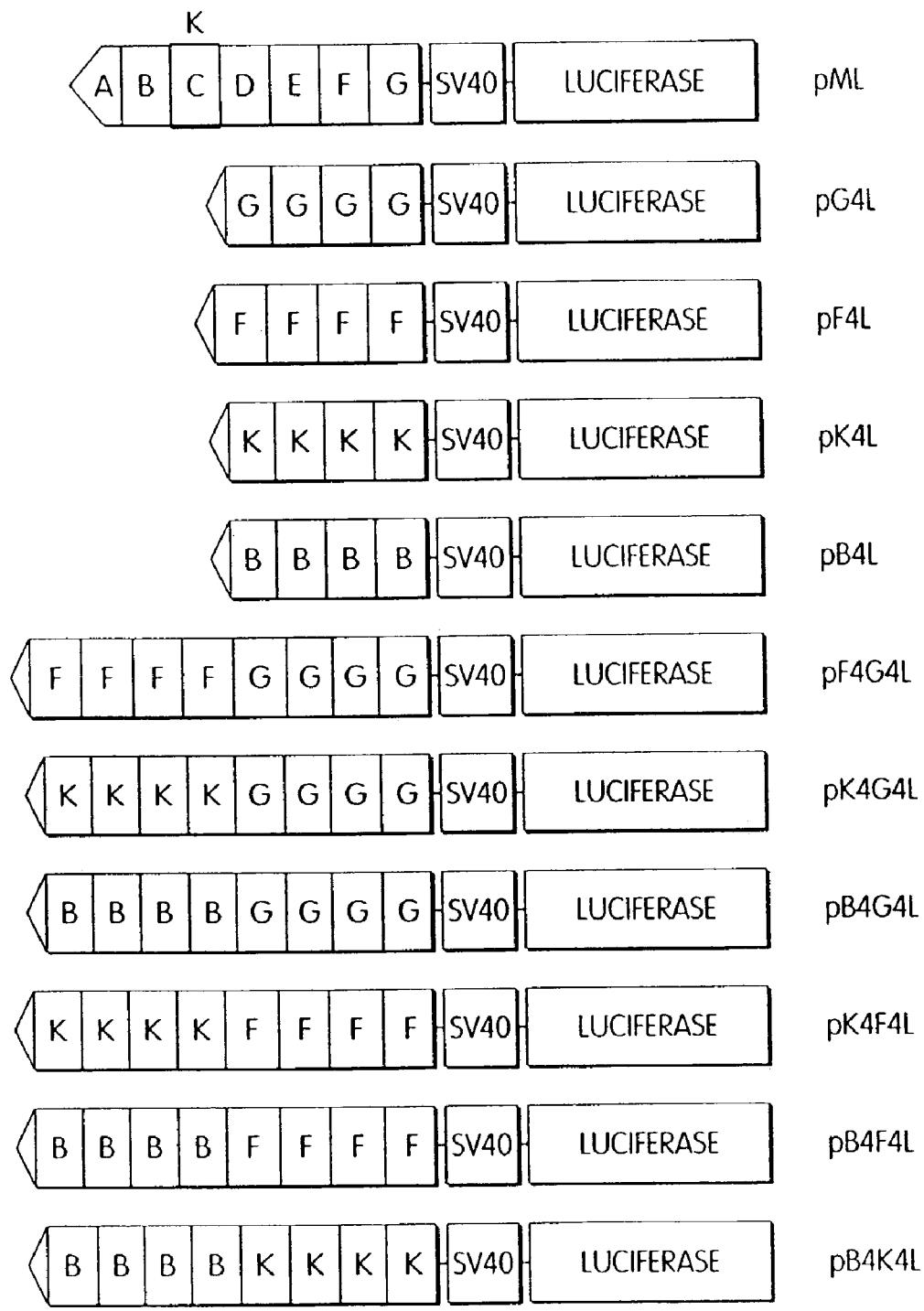
FIG. 7A shows a map for the MAR fragment-linked luciferase gene constructs. The pML construct shows the natural MAR sequence, arbitrarily segmented in parts A, B, C, D, E, F, G and K, the SV40 early promoter, as indicated by the SV40-labelled box, and the luciferase reporter transgene. Construct pLM has the luciferase transgene placed between the SV40 promoter and natural MAR sequence. Other constructs shown in Example 7 pML contain multimerized portions of the MAR element as indicated. The DNA sequence of the MAR segments is provided in Example 7.
Figure 7B:
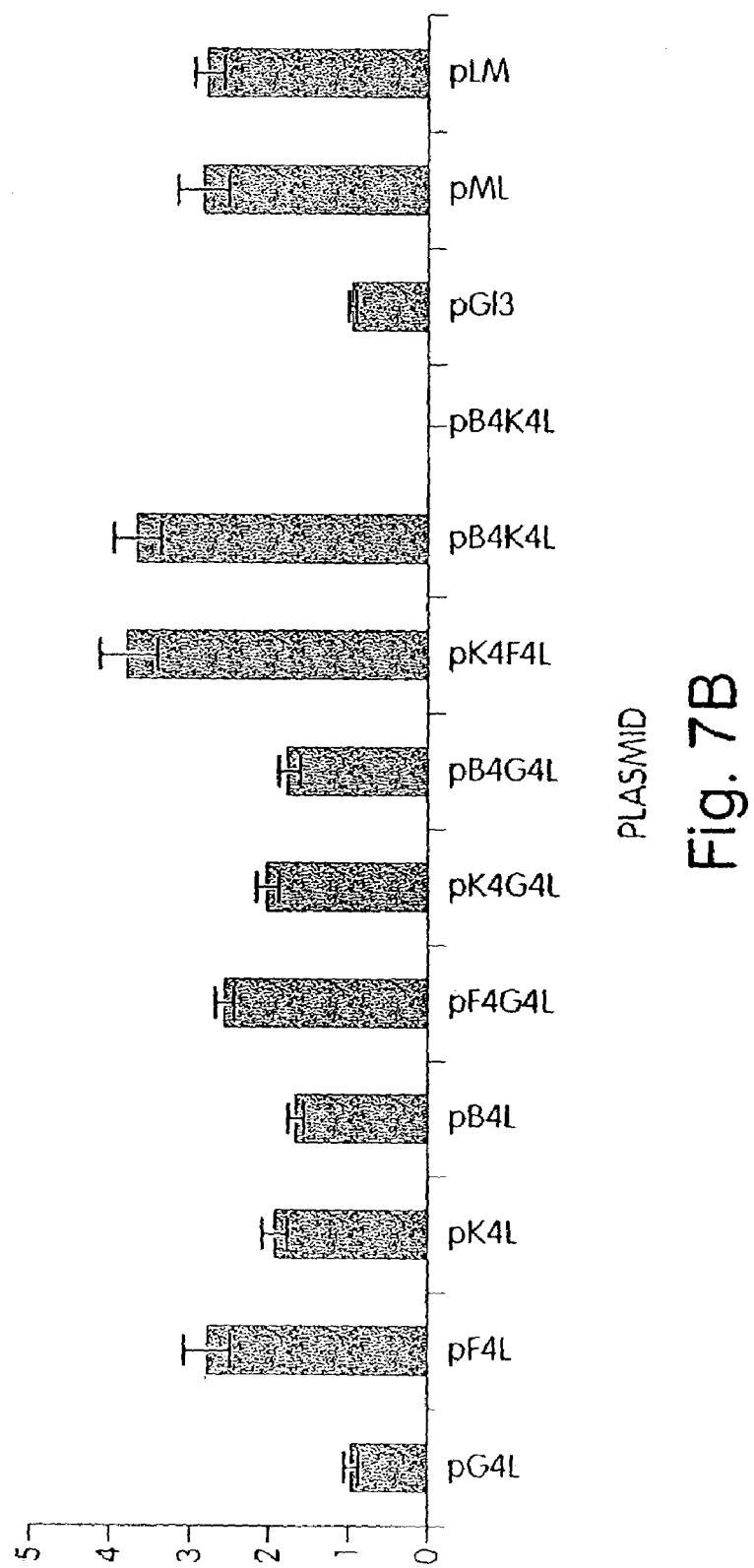
FIG. 7B shows the results of luciferase measurements performed with extracts of cells containing a reporter construct lacking MAR sequence (pGL3) or derivatives containing in cis one copy of the natural MAR sequences (pML, pLM), or containing multimerized MAR elements as indicated in part (A). Analyses were performed with G-418 selected populations (polyclonal pools of stably transfected CHO cells), as in the art. The results represent data from two independent sets of experiments.

The MAR elements of the invention include fragments of MAR elements, such as fragments of SEQ ID NO:1. FIG. 7 demonstrates that four copies of the MAR fragment F (pF4L) display similar expression as those obtained with the longer, natural MAR sequences. Other fragments display lower (K, B) or no (G) expression. When two distinct MAR element fragments are combined, in PK4F4L or in pB4K4L, higher expression than the full length MAR element (SEQ ID NO: 1) is obtained. Thus, particular combinations of MAR element fragments are prefered in order to modulate transgene expression, depending on whether a small size or maximal expression is desired.

Materials and Methods:

Construction of pLuc-based Plasmids (SV40 Promoter-based Luciferase Gene Construct):

The various MAR fragments (i.e. B, K, F and G) were amplified by polymerase chain reaction using pUC-BI-XI as template with specific primer sets that introduced a BglII and a BamHI site in 5'- and 3'-end, respectively. After release of the latter restriction sites, the fragments were self-ligated in presence of BglII and BamHI. The dimer- and tetramer-repeats in direct orientation were cloned between the BglII-BamHI sites of pGL3-Control (Promega). To construct the pLuc-based plasmids, the various tetramers were excised as BglII-BamHI fragments and subcloned into plasmid pGL3-Control at the BglII site. For pF4G4L, pK4G4L and pB4G4L, the F4, K4 and B4 fragments were cloned into the BglII site of plasmid pG4L, respectively. The plasmids pK4F4L and pB4F4L were constructed by cloning K4 and B4 in pF4L and pB4K4L was generated by cloning B4 into the BglII site of pK4L.

Cell Culture and Stable Gene Transfer:

CHO DG44 cells were grown as described (See supra). The above pLuc-derivatives and pGL3-Control were transfected in parallel in order to create the recipient cell lines for expression studies of MAR fragments vectors and control vectors. For transfection, cells were seeded in 24-well plates at 1.3 E5 cell/well and allowed to attach for 16H. After washing with PBS, cells were transfected in triplicate with mixes in a final volume of 81 µl OptiMEM (Gibco, Life Sciences). Typically, the mixes contained 0.327 pmol of MAR-derivative plasmids and pGL3-Control and 23,4 fmol of pSVneo. In a polystyrene tube, 77 µl OptiMEM were combined with 4 µl of LipofectAMIN2000 (Gibco, Life Sciences) per triplicate and incubated for 5 min. Subsequently, the DNA and Lipofectamin2000 mixes were combined in a polystyrene tube. After 15 min at room temperature, the mixes were supplemented with 1 ml OptiMEM per triplicate and 300 µl of these mixes were aliquoted into each well. Cells were exposed to the transfection mixes for 3H. Thereafter, 1 ml of DMEM supplemented with 110% FBS (Gibco, Life Sciences) was added to each well. Cells were passaged 48H post-transfection and the triplicates pooled into T-75 containing 14 ml of medium supplemented with 750 µg G-418. The medium was replaced every 4 days. Cells were passaged two weeks post-transfection.

Extract Preparation and Enzymatic Measurements:

Triplicate 250 µl samples of cell suspension were harvested by centrifugation, washed with PBS, and incubated with 100 µl lysis buffer for 20 min at room temperature. 20 µl of extracts were transfered to a flat bottom 96 well for subsequent luciferase measurement. 5 µl of extracts were used for protein determination by Bradford.

Relative light units were calculated by normalizing luciferase for Bradford measurement. Data points represent the average of the triplicate of two independent transfection experiments.

```
Sequences of MAR fragments:
1. Fragment B (MAR region: bp 374-765)
BglII-
GATCTgcaaattgcttaacagtctcctaaaggctgaa    (SEQ ID NO:6)

aaaaaggaacccatgaaagctaaaagttatgcagtat ttcaagtataacatctaaaaatgatgaaacgatccct aaaggtagagattaactaagtacttctgctgaaaatg tattaaaatccgcagttgctaggataccatcttacct tgagaaatacaggtctccggcaacgcaacattcagca gactctttggcctgctggaatcaggaaactgcttact atatacacatataaaatcctttggagttgggcattct gagagacatccatttcctgacattttgcagtgcaatc
```

-continued tgcattccaactcagacaagctcccatgctgtatttc aaagccatttcttgaatagtttGGATC
-BamHI 2. Fragment K (MAR region: bp 840–1230)
Bgl II-
GATCTaagtcagcagcgctggtaatcttcataaaaat (SEQ ID NO:7)

gtaactgttttccaaataggaatgtatttcacttgta aaacacctggtccttttatattactttttttttttt taaggacacctgcactaatttgcaatcacttgtattt ataaaagcacacgcactcctcattttcttacatttga agatcagcagaatgtctctttcataatgtaataatca tatgcacagtttaaaatattttctattacaaaataca gtacacaagagggtgaggccaaagtctattacttgaa tatattccaaagtgtcagcactgggggtgtaaaatt acattacatggtatgaataggcggaattcttttacaa ctgaaatgctcgatttcGGATC
-BamHI 3. Fragment F (MAR region: bp 1975–2421)
Bgl II-
GATCTacaacacaagaaccaacgacagactgcatata (SEQ ID NO:8)

aaattctataaataaaaataggagtgaagtctgtttg acctgtacacacagagcatagagataaaaaaaaaagg aaatcaggaattacgtatttctataaatgccatatat ttttactagaaacacagatgacaagtatatacaacat gtaaatccgaagttatcaacatgttaactaggaaaac atttacaagcatttgggtatgcaactagatcatcagg taaaaaatcccattagaaaatctaagcctcgccagt ttcaaaggaaaaaaaccagagaacgctcactacttca aaggaaaaaaataaagcatcaagctggcctaaactt aataaggtatctcatgtaacaacagctatccaagctt tcaagccacactataaataaaaacctcaagttccgat caacgttggatcccgGGATC
-BamHI 4. Fragment G (MAR region: bp 2485–2906)
BglII-
GATCTgggctgtacagtttccaaaaggttcttcttttt (SEQ ID NO:9)

gaagaaatgtttctgacctgtcaaaacatacagtcca gtagaaattttactaagaaaaaagaacaccttactta aaaaaaaaaacaacaaaaaaaacaggcaaaaaaacc tctcctgtcactgagctgccaccacccaaccaccacc tgctgtgggctttgtctcccaagacaaaggacacaca gccttatccaatattcaacattacttataaaaacgct gatcagaagaaataccaagtatttcctcagagactgt tatatcctttcatcggcaacaagagatgaaatacaac agagtgaatatcaaagaaggcggcaggagccaccgtg -continued gcaccatcaccgggcagtgcagtgcccaactgccgtt ttctgagcacgcataggaaGGATC-BamHI

REFERENCES

Agarwal, M., Austin, T., Morel, F., Chen, J., Bohnlein, E., and Plavec, I. (1998). Scaffold attachment region-mediated enhancement of retroviral vector expression in primary T cells. J Virol 72, 3720–3728.

Allen, G., Hall, G. J., Michalowski, S., Newman, W., Spiker, S., Weissinger, A., and Thompson, W. (11996). High-level transgene expression in plant cells: effects of a strong scaffold attachment region from tobacco. Plant Cell 8, 899–913.

Bell, A., and Felsenfeld, G. (1999). Stopped at the border: boundaries and insulators. Curr Opin Genet Dev 9, 191–198.

Bi, X., and Broach, J. (1999). UASrpg can function as a heterochromatin boundary element in yeast. Genes Dev 13, 1089–1101.

Bode, J., Benham, C., Knopp, A., and Mielke, C. (2000). Transcriptional augmentation: modulation of gene expression by scaffold/matrix-attached regions (S/MAR elements). Crit Rev Eukaryot Gene Expr 10, 73–90.

Bode, J., Schlake, T., Rios-Ramirez, M., Mielke, C., Stengert, M., Kay, V., and Klehr-Wirth, D. (11995). Scaffold/matrix-attached regions: structural properties creating transcriptionally active loci. In Structural and Functional Organization of the Nuclear Matrix, R. Berezney and K. Jeon, eds. (San Diego: Academic Press, Inc.), pp. 389–454.

Boussif, O., Lezoualc'h, F., Zanta, M., Mergny, M., Scherman, D., Demeneix, B., and Behr, J.-P. (1995). A versatile vector for gene and oligonucleotide transfer into cells in culture and in vivo: polyethylenimine. Proc Natl Acad Sci USA 92, 7297–7301.

Castilla, J., Pintado, B., Sola, I., Sanchez-Morgado, J., and Enjuanes, L. (1998). Engineering passive immunity in transgenic mice secreting virus-neutralizing antibodies in milk. Nat Biotechnol 16, 349–354.

Cuvier, O., Hart, C., and Laemmli, U. (1998). Identification of a class of chromatin boundary elements. Mol Cell Biol 18, 7478–7486.

Fussenegger, M., Bailey, J., Hauser, H., and Mueller, P. (1999). Genetic optimization of recombinant glycoprotein production by mammalian cells. Trends Biotechnol 17, 35–42.

Grosveld, F. (1999). Activation by locus control regions? Curr Opin Genet Dev 9, 152–157.

Hart, C., and Laemmli, U. (1998). Facilitation of chromatin dynamics by SARs. Curr Opin Genet Dev 8, 519–525.

Imhof, M., Chatellard, P., and Mermod, N. (2000). A regulatory network for the efficient control of transgene expression. J Gene Med 2, 107–116.

Jenuwein, T., Forrester, W., Fernandez-Herrero, L., Laible, G., Dull, M., and Grosschedl, R. (1997). Extension of chromatin accessibility by nuclear matrix attachment regions. Nature 385, 269–272.

Jordan, M., Schallhorn, A., and Wurm, F. (1996). Transfecting mammalian cells: optimization of critical parameters affecting calcium-phosphate precipitate formation. Nucleic Acids Res 24, 596–601.

Kalos, M., and Fournier, R. (1995). Position-independent transgene expression mediated by boundary elements from the apolipoprotein B chromatin domain. Mol Cell Biol 15, 198–207.

Kaufman, R., and Sharp, P. (1982). Amplification and expression of sequences cotransfected with a modular dihydrofolate reductase complementary DNA gene. J Mol Biol 159, 601–621.

Klehr, D., Maass, K., and Bode, J. (1991). Scaffold-attached regions from the human interferon β domain can be used to enhance the stable expression of genes under the control of various promoters. Biochemistry 30, 1264–1270.

MacGregor, G., and Caskey, C. (1989). Construction of plasmids that express E. coli β-galactosidase in mammalian cells. Nucleic Acids Res 17, 2365.

McKnight, R., Shamay, A., Sankaran, L., and Wall, R. (1992). Matrix-attachment regions can impart position-independent regulation of a tissue-specific gene in transgenic mice. Proc Natl Acad Sci USA 89, 6943–6947.

Miescher, S., Zahn-Zabal, M., Jesus, M. d., Moudry, R., Fisch, I., Vogel, M., Imboden, M., Mermod, N., Stadler, B., Amstutz, H., and Wurm, F. CHO expression of a novel human recombinant IgGI anti-Rh D antibody isolated by phage panning on bromelin treated rhesus $D^{VI+}$ red blood cells. (in press).

Neff, T., Shotkoski, F., and Stamatoyannopoulos, G. (1997). Stem cell gene therapy, position effects and chromatin insulators. Stem Cells 15, 265–271.

Ortiz, B., Cado, D., Chen, V., Diaz, P., and Winoto, A. (1997). Adjacent DNA elements dominantly restrict the ubiquitous activity of a novel chromatin-opening region to specific tissues. EMBO J 16, 5037–5045.

Pawliuk, R., Bachelot, T., Raftopoulos, H., Kalberer, C., Humphries, R., Bank, A., and Leboulch, P. (1998). Retroviral vectors aimed at the gene therapy of human beta-globin gene disorders. Ann N Y Acad Sci 850, 151–162.

Phi-Van, L., Kries, J. v., Ostertag, W., and Strätling, W. (1990). The chicken lysozyme 5' matrix attachment region increases transcription from a heterologous promoter in heterologous cells and dampens position effects on the expression of transfected genes. Mol Cell Biol 10, 2302–2307.

Phi-Van, L., and Strätling, W. (1988). The matrix attachment regions of the chicken lysozyme gene co-map with the boundaries of the chromatin domain. EMBO J 7, 655–664.

Piechaczek, C., Fetzer, C., Baiker, A., Bode, J., and Lipps, H. (1999). A vector based on the SV40 origin of replication and chromosomal S/MARs replicates episomally in CHO cells. Nucleic Acids Res 27, 426–428.

Poljak, L., Seum, C., Mattioni, T., and Laemmli, U. (1994). SARs stimulate but do not confer position independent gene expression. Nucleic Acids Res 22, 4386–4394.

Schimke, R., Brown, P., and Kaufman, R. (1982). Gene amplification and drug resistance in mammalian cells. Natl Cancer Inst Monogr 60, 79–86.

Stief, A., Winter, D., Strätling, W., and Sippel, A. (1989). A nuclear DNA attachment element mediates elevated and position-independent gene activity. Nature 341, 343–345.

Talbot, D., Descombes, P., and Schibler, U. (1994). The 5' flanking region of the rat LAP (C/EPBβ) gene can direct high-level, position-independent, copy number-dependent expression in multiple tissues in transgenic mice. Nucleic Acids Res 22, 756–766.

Udvardy, A. (1999). Dividing the empire: boundary chromatin elements delimit the territory of enhancers. EMBO J 18, 1–8.

Urlaub, G., Käs, E., Carothers, A., and Chasin, L. (1983). Deletion of the diploid dihydrofolate reductase locus from cultured mammalian cells. Cell 33, 405–412.

Walters, M., Fiering, S., Bouhassira, E., Scalzo, D., Goeke, S., Magis, W., Garrick, D., Whitelaw, E., and Martin, D. (1999). The chicken beta-globin 5'HS4 boundary element blocks enhancer-mediated suppression of silencing. Mol Cell Biol 19, 3714–3726.

Wang, Y., DeMayo, F., Tsai, S., and O'Malley, B. (1997). Ligand-inducible and liver-specific target gene expression in transgenic mice. Nature Biotech 15, 239–243.

Wells, K., Foster, J., Moore, K., Pursel, V., and Wall, R. (1999). Codon optimization, genetic insulation, and an rtTA reporter improve performance of the tetracycline switch. Transgenic Res 8, 371–381.

Wurm, F., Pallavicini, M., and Arathoon, R. (1992). Integration and stability of CHO amplicons containing plasmid sequences. Dev Biol Stand 76, 69–82.

OTHER EMBODIMENTS

It is to be understood that, while the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. A method for transfecting a eukaryotic cell to incorporate a desired gene or portion thereof into said cell wherein the method comprises co-transfecting the cell with unlinked vectors, said unlinked vectors comprising: a first vector comprising a first promoter and a first heterologous gene encoding the desired gene or portion thereof under the transcriptional control of the first promoter, and on first chromatin element, a second unlinked vector comprising a second chromatin element; and a third vector comprising a third vector comprising a second promoter and a second heterologous gene, wherein the chromatin elements are selected from the group consisting of boundary elements, matrix attachment regions, locus control regions and universal chromatin opening elements.

2. The method of claim 1, wherein said first, second and third vectors are introduced in a molar ratio of between about 1:1.75:5.5 to about 1:1.75:11.

3. The method of claim 1, wherein the second chromatin element is the same as the first chromatin element.

4. The method of claim 1, wherein said desired gene is selected from the group consisting of a structural gene and a regulatory gene.

5. The method of claim 1, wherein the desired gene encodes a polypeptide selected from the group consisting of an antibody, antibody fragment, an antibody light chain and an antibody heavy chain.

6. The method of claim 1, wherein the desired gene encodes for a human anti-Rhesus D IgG antibody.

7. The method of claim 1, wherein the first vector further comprises a regulatable gene expression element that permits regulation of expression of the desired gene product by administration of an exogenous molecule.

8. The method of claim 7, wherein the regulatable gene expression element is the Tet-regulatable element.

9. The method of claim 1, further comprising contacting said cell with butyrate.

10. The method of claim 9, wherein the concentration of said butyrate is about 10 mM.

11. The method of claim 1, wherein said first chromatin element is located 5' to said promoter and said first heterologous gene.

12. The method of claim 1, wherein said first chromatin element is located 3' to said promoter and said first heterologous gene.

* * * * *